(12) United States Patent
Yodfat et al.

(10) Patent No.: US 10,265,464 B2
(45) Date of Patent: *Apr. 23, 2019

(54) MANUALLY OPERABLE PORTABLE INFUSION DEVICE

(71) Applicant: Roche Diabetes Care, Inc., Indianapolis, IN (US)

(72) Inventors: Ofer Yodfat, Maccabim-Reut (IL); Danna Perlman, Haifa (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 624 days.

This patent is subject to a terminal disclaimer.

(21) Appl. No.: 14/884,325

(22) Filed: Oct. 15, 2015

(65) Prior Publication Data
US 2016/0030664 A1 Feb. 4, 2016
US 2019/0001052 A9 Jan. 3, 2019

Related U.S. Application Data

(63) Continuation of application No. 14/551,542, filed on Nov. 24, 2014, now Pat. No. 9,192,713, which is a
(Continued)

(51) Int. Cl.
*A61M 5/168* (2006.01)
*A61M 5/142* (2006.01)
(Continued)

(52) U.S. Cl.
CPC ...... *A61M 5/1424* (2013.01); *A61M 5/14244* (2013.01); *A61M 5/14248* (2013.01);
(Continued)

(58) Field of Classification Search
CPC .......... A61M 5/14244; A61M 5/14248; A61M 2005/14268
See application file for complete search history.

(56) References Cited

U.S. PATENT DOCUMENTS

| 3,771,694 A | 11/1973 | Kaminski |
| 4,498,843 A | 2/1985 | Schneider et al. |

(Continued)

FOREIGN PATENT DOCUMENTS

| EP | 362484 A3 | 8/1990 |
| WO | 9956803 A1 | 11/1999 |

(Continued)

*Primary Examiner* — Laura A Bouchelle
(74) *Attorney, Agent, or Firm* — Dinsmore & Shohl, LLP

(57) ABSTRACT

A portable therapeutic fluid delivery device and a method for delivering a therapeutic fluid into a body of a patient are provided. In one aspect the therapeutic fluid delivery device and the method can be implemented using at least one housing securable to the body of the patient, a reservoir coupled to the at least one housing, a therapeutic fluid dispensing mechanism, a memory component, a controller, at least one bolus delivery button configured to signal the controller to initiate the delivery of the therapeutic fluid into the body of the patient; and, an inadvertent initiation prevention mechanism adapted for preventing the patient from activating the at least one bolus delivery button.

16 Claims, 24 Drawing Sheets

Related U.S. Application Data continuation of application No. 13/621,723, filed on Sep. 17, 2012, now Pat. No. 8,894,632, which is a continuation of application No. 12/452,763, filed as application No. PCT/IL2008/001001 on Jul. 20, 2008, now Pat. No. 8,267,921.

(60) Provisional application No. 60/961,527, filed on Jul. 20, 2007.

(51) Int. Cl.
*A61M 5/172* (2006.01)
*A61M 5/14* (2006.01)

(52) U.S. Cl.
CPC .............. *A61M 5/168* (2013.01); *A61M 5/172* (2013.01); *A61M 2005/1405* (2013.01); *A61M 2205/17* (2013.01); *A61M 2205/3576* (2013.01); *A61M 2205/52* (2013.01)

(56) References Cited

U.S. PATENT DOCUMENTS

| | | | |
|---|---|---|---|
| 4,657,486 A | 4/1987 | Stempfle et al. | |
| 5,957,895 A | 9/1999 | Sage et al. | |
| 6,485,461 B1 | 11/2002 | Mason et al. | |
| 6,589,229 B1 | 7/2003 | Connelly et al. | |
| 6,702,779 B2 | 3/2004 | Connelly et al. | |
| 6,723,072 B2 | 4/2004 | Flaherty et al. | |
| 6,740,059 B2 | 5/2004 | Flaherty | |
| 6,749,587 B2 | 6/2004 | Flaherty | |
| 7,713,262 B2 * | 5/2010 | Adams | A61M 5/14248 604/890.1 |
| 7,935,104 B2 | 5/2011 | Yodfat et al. | |
| 8,267,921 B2 * | 9/2012 | Yodfat | A61M 5/14248 604/151 |
| 8,894,632 B2 | 11/2014 | Yodfat et al. | |
| 2003/0160683 A1 | 8/2003 | Blomquist | |
| 2004/0162518 A1 | 8/2004 | Connelly et al. | |
| 2005/0065466 A1 | 3/2005 | Vedrine | |
| 2005/0171512 A1 | 8/2005 | Flaherty | |
| 2007/0106218 A1 | 5/2007 | Yodfat et al. | |
| 2007/0282269 A1 | 12/2007 | Carter et al. | |
| 2008/0051709 A1 * | 2/2008 | Mounce | A61M 5/1413 604/131 |

FOREIGN PATENT DOCUMENTS

| | | |
|---|---|---|
| WO | 2004052429 A1 | 6/2004 |
| WO | 2009016636 A2 | 2/2009 |
| WO | 2008139458 A3 | 3/2009 |

* cited by examiner

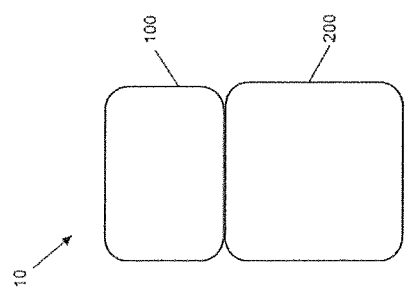
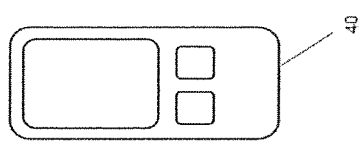
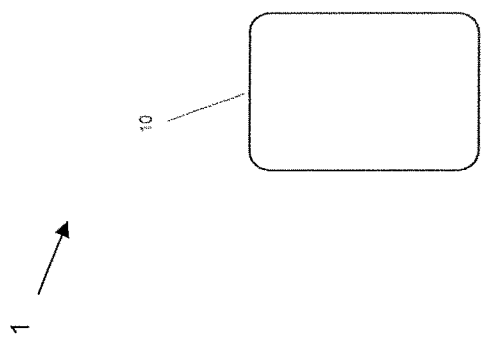

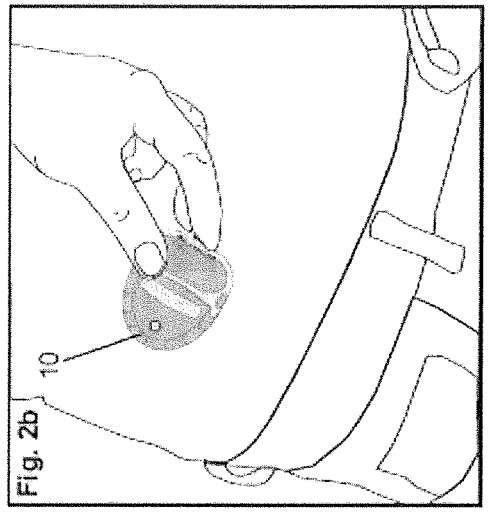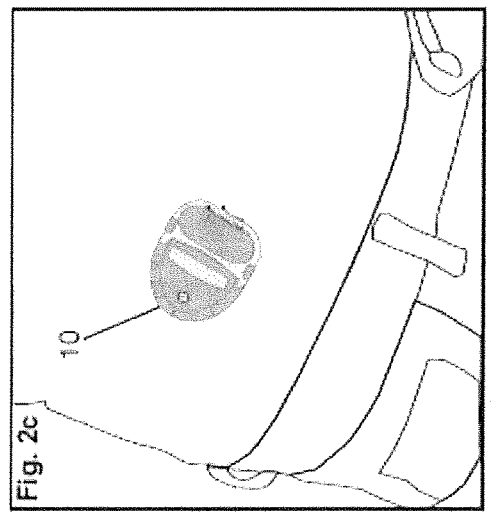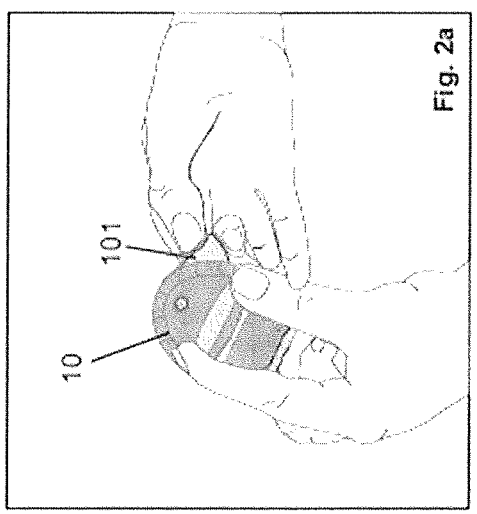

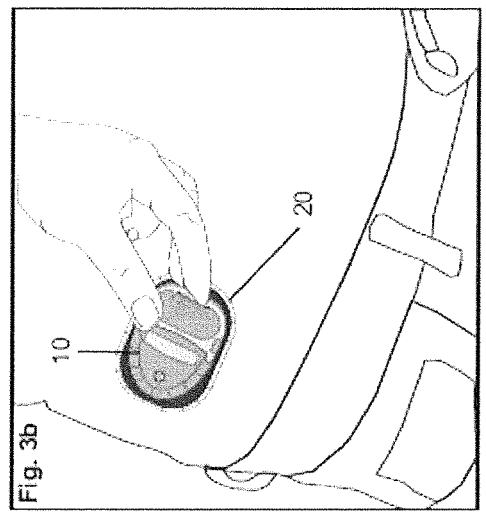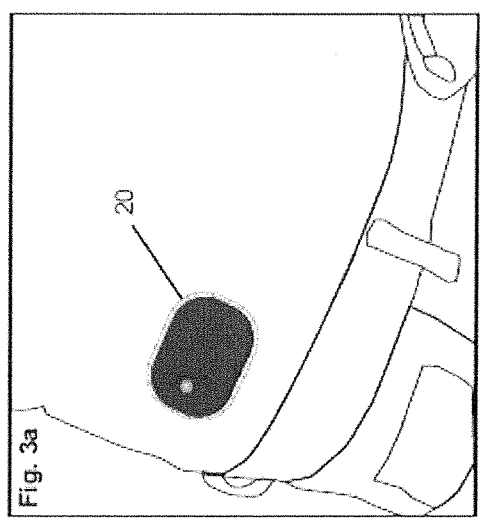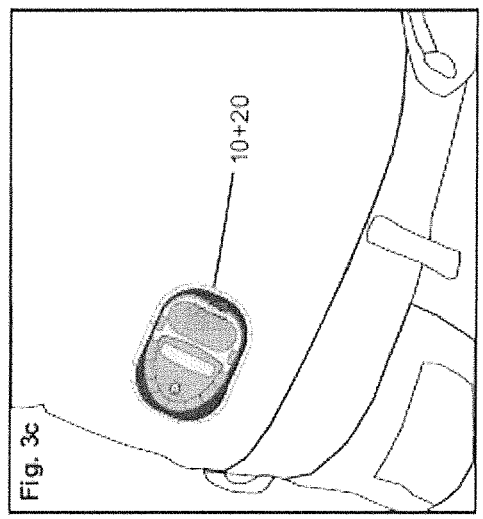

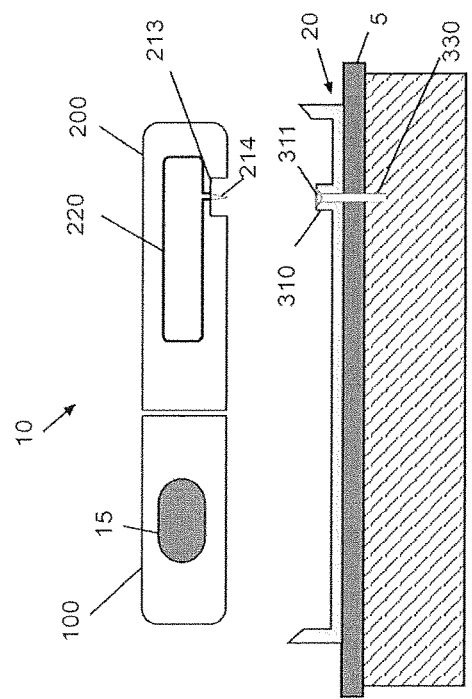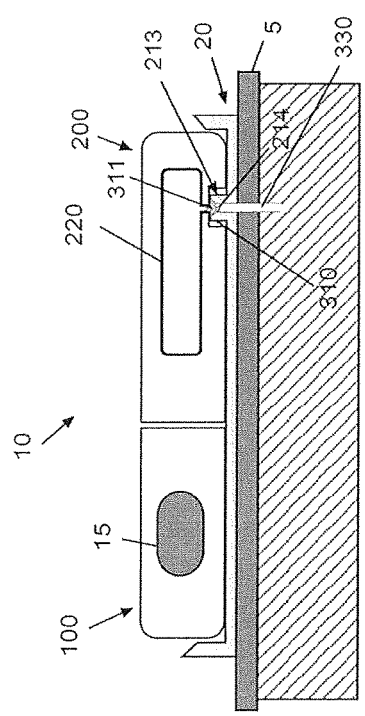
Fig. 5a
Fig. 5b

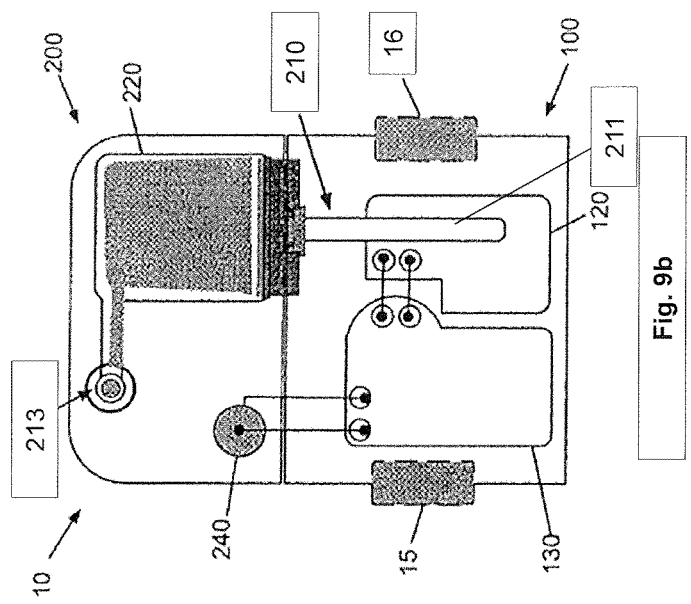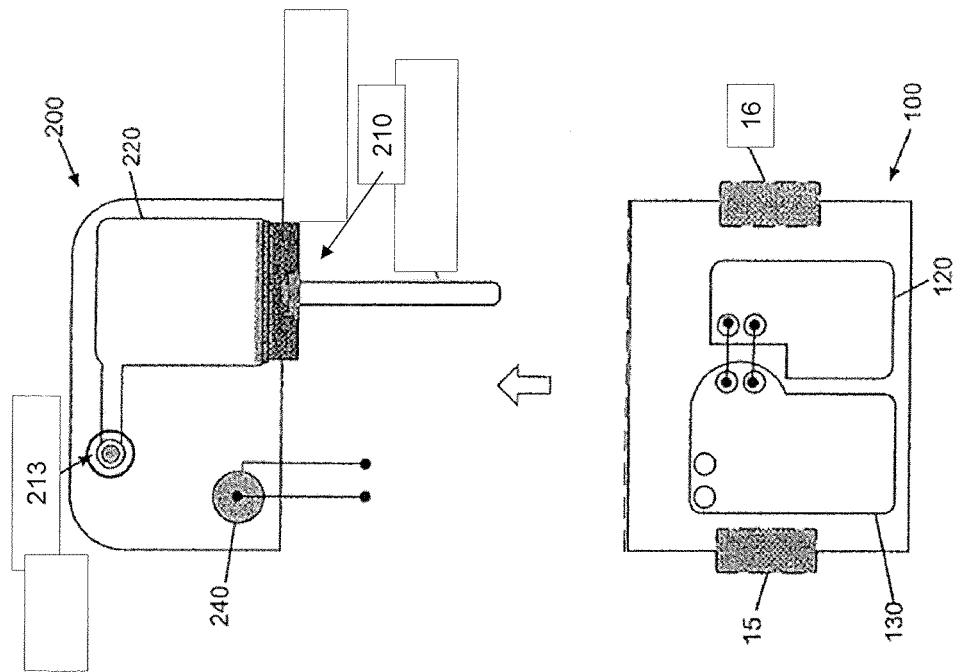

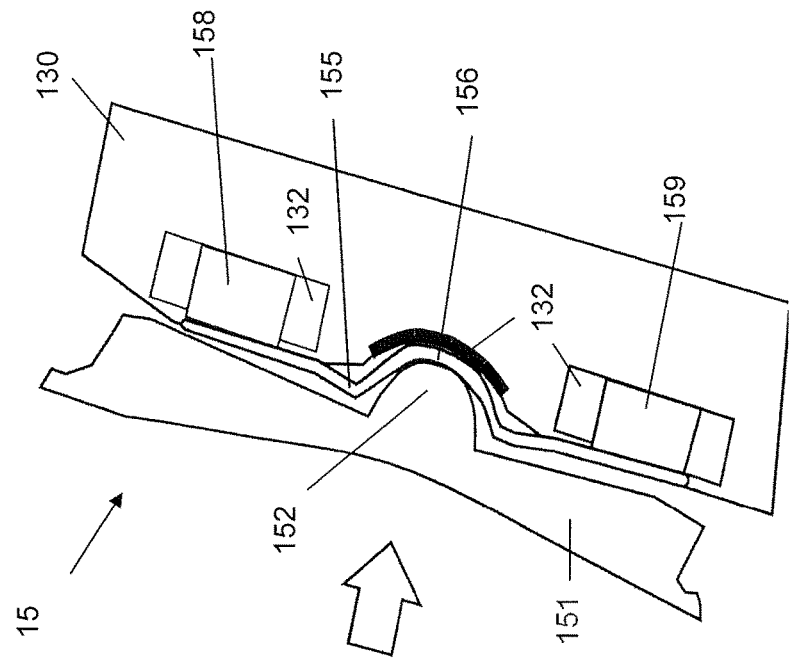
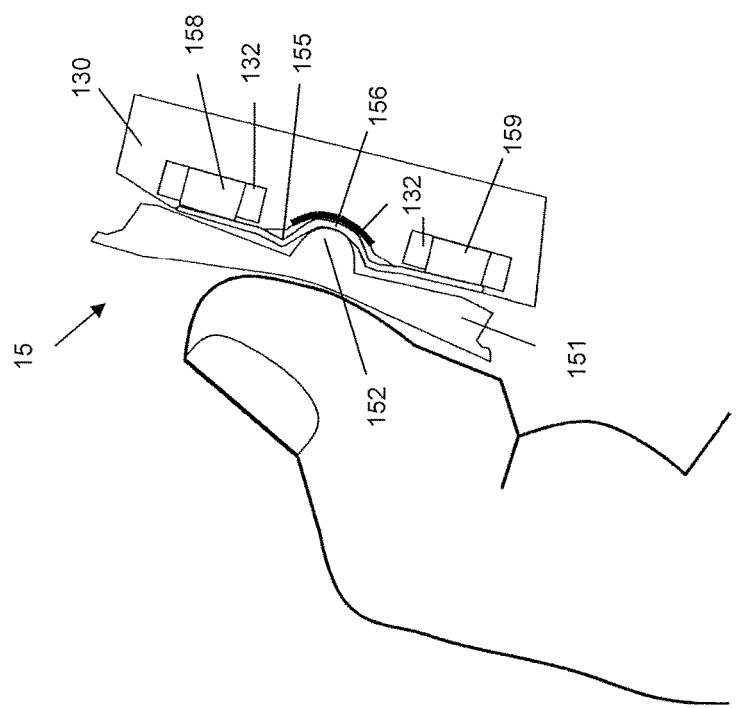
Fig. 14b
Fig. 14a

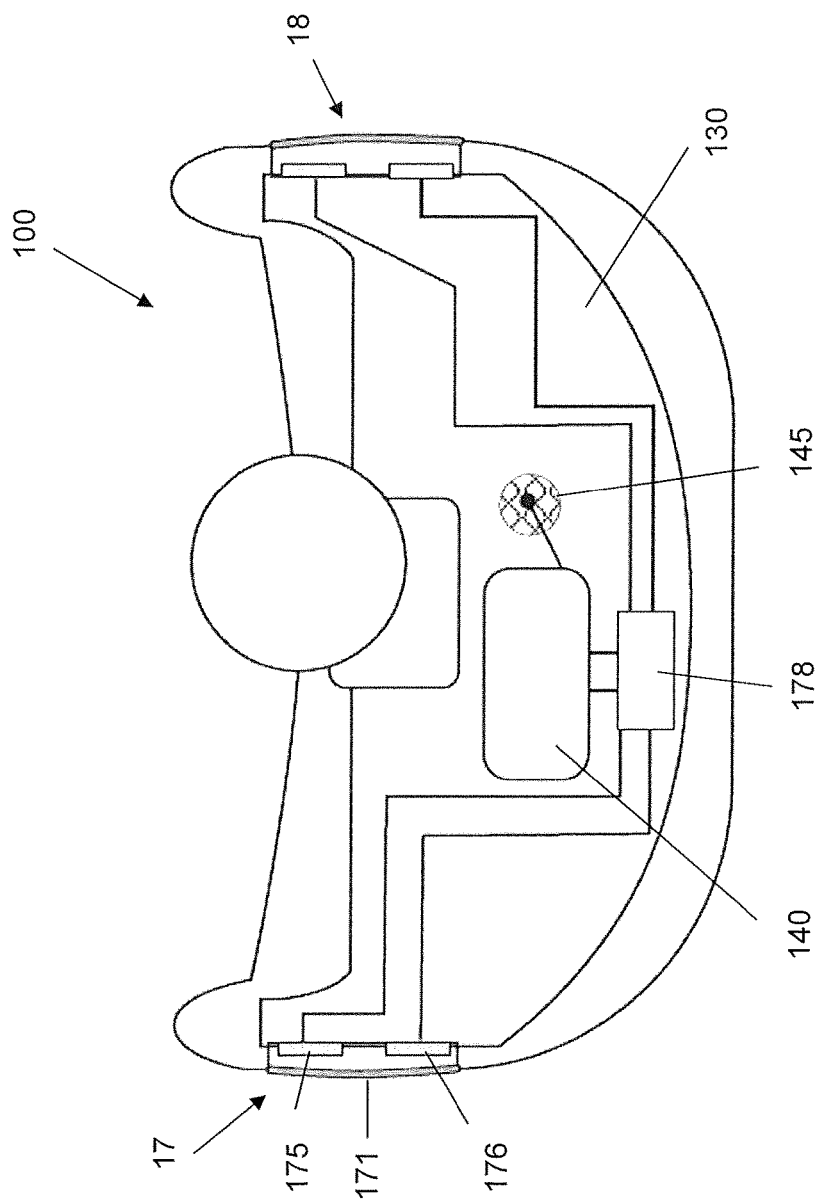

MANUALLY OPERABLE PORTABLE INFUSION DEVICE

CROSS-REFERENCE TO RELATED APPLICATIONS

The present application is a continuation of pending U.S. patent application Ser. No. 14/551,542 filed on 24 Nov. 2014, which is a continuation of pending U.S. patent application Ser. No. 13/621,723, now U.S. Pat. No. 8,894,632 issued 25 Nov. 2014, which is a continuation of U.S. patent application Ser. No. 12/452,763, now U.S. Pat. No. 8,267,921 issued 18 Sep. 2012, which is a 35 U.S.C. §371 national stage entry of PCT/IL2008/001001, which has an international filing date of 20 Jul. 2008 and claims priority to U.S. Provisional Patent Application No. 60/961,527, filed on 20 Jul. 2007. The present application incorporates herein by reference the disclosure of each of the above-referenced applications in their entirety.

FIELD OF THE INVENTION

A system, device and a method for sustained medical infusion of fluids are provided. More particularly, a miniature portable therapeutic fluid delivery device that can be attached to a patient's body and accurately dispense fluids to the patient's body is described. In some implementations, the device can be activated using one or more buttons coupled to electronic components.

BACKGROUND OF THE INVENTION

Medical treatment of several illnesses requires continuous drug infusion into various body compartments, such as subcutaneous and intra-venous injections. Diabetes mellitus patients, for example, require the administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

The 1st generation of portable infusion pumps disclosed "pager-like" devices with a reservoir contained within the device's housing. In such 1st generation devices, a long tube delivers insulin from the pump attached to a patient's belt to a remote insertion site. Both basal and bolus volume deliveries in these "pager-like" devices are controlled via a set of buttons provided on the device. Such devices are disclosed, for example, in U.S. Pat. Nos. 3,771,694, 4,657,486 and 4,498,843. These devices represent a significant improvement over multiple daily injections, but nevertheless, they all suffer from several major drawbacks, among which are the large size and weight of the device.

These uncomfortable bulky devices are rejected by the majority of diabetic insulin users, since they disturb regular activities, such as sleeping and swimming. In addition, the delivery tube excludes some optional remote insertion sites, like buttocks, arms and legs. To avoid the consequences of long delivery tube, a 2nd generation of pumps was proposed. As described in the prior art, the 2nd generation systems include a remote controlled skin adherable device with a housing having a bottom surface adapted for contact with the patient's skin, a reservoir disposed within the housing, and an injection needle adapted for communication with the reservoir. These skin adherable devices should be discarded every 2-3 days to avoid irritation and infection. This paradigm was described, for example, in U.S. Pat. Nos. 5,957,895, 6,589,229, 6,740,059, 6,723,072 and 6,485,461. However, these 2nd generation devices also have limitations: they are bulky and expensive. The high selling price is due to the high production and accessory costs. Moreover, such systems are expensive for users since they must be discarded every 2-3 days, including the relatively expensive components, such as the driving mechanism and other electronics.

Another major drawback of these 2nd generation skin adherable devices concerns the remote controlled drug administration. The users are totally dependent on the remote control and cannot initiate a bolus delivery if the remote control is not at hand, lost or has malfunctioned (practically, the patient cannot eat).

In some 2nd generation devices, a manual bolus button is disclosed, for example in U.S. Pat. No. 6,740,059, assigned to Insulet Corporation. When pressed, the spring loaded button moves a release finger away from a bolus delivery tube, thus enabling the delivery of a fixed amount of fluid from a bolus volume accumulator to the exit port of the device. This system has several drawbacks:

1. Unsafe: a life-threatening, unwanted bolus can be delivered by unintentional pressing of the button.
2. Not tailored to patient needs: a one size accumulator allows one bolus dose per button press. Thus, for example, if the accumulator volume is 0.2 units of insulin, a toddler that needs an average bolus dose of 1 unit has to press the button 5 times; however an adult that requires an average bolus dose of 6 units has to press the button 30 times. If, for example, the accumulator volume is 1 unit, the same adult needs 6 button presses but it limits most kids from using manual bolus delivery.
3. Prolonged manual bolus administration: the user has to wait for the accumulator to be refilled before the next consecutive bolus. For example, if 10 presses are required and the filling time is 0.5 minutes, the bolus administration time is 5 minutes.
4. Enlargement of the device's overall size: the employment of two reservoirs, one for basal delivery and one for bolus delivery, as well as two separate tubes and additional mechanical components (e.g. spring) requires enlargement of the device's overall size.

A mechanical bolus button, suffering from the same abovementioned drawbacks, was also disclosed in U.S. Patent Application No. 2004/0162518, and U.S. Pat. No. 6,702,779 assigned to Becton, Dickinson and Company.

A 3rd generation skin adherable device was devised to avoid the cost issues of the 2nd generation and to extend patient customization. An example of such a device was described in co-owned/co-pending U.S. patent application Ser. No. 11/397,115 and International Patent Application No. PCT/IL06/001276, disclosers of which are incorporated herein by reference in their entireties. This 3rd generation device contains a remote control unit and a skin adherable dispensing patch unit (also referred to as "dispensing unit" or "dispensing patch") that is comprised of two parts:

Reusable part—including the driving mechanism, fluid dispensing mechanism, electronics and other relatively expensive components.

Disposable part—including inexpensive, disposable components such as reservoir, tube and batteries, and an outlet port.

This 3rd generation device/system provides a cost-effective skin adherable infusion device/system and allows diverse usage such as various reservoir sizes, various needle and cannula types, etc.

This 3rd generation skin adherable device, similarly to 2nd generation devices, can also be remotely controlled. However, it is desirable that manual initiation of fluid delivery will be possible when the remote control unit is not at hand (or not included), for at least one of basal and bolus drug delivery.

SUMMARY OF THE INVENTION

A portable therapeutic fluid delivery device and a method for delivering a therapeutic fluid into a body of a patient are provided. In one aspect the therapeutic fluid delivery device and the method can be implemented using at least one housing securable to the body of the patient; a reservoir for containing the therapeutic fluid, said reservoir coupled to the at least one housing; a therapeutic fluid dispensing mechanism coupled to said reservoir; a memory component adapted for storing a value corresponding to a therapeutic fluid delivery dose; a controller adapted for initiating a delivery of the therapeutic fluid by activating the therapeutic fluid dispensing mechanism, said controller further adapted for limiting the delivery of the therapeutic fluid based on the value stored in the memory component; at least one bolus delivery button configured to signal the controller to initiate the delivery of the therapeutic fluid into the body of the patient; and, an inadvertent initiation prevention mechanism adapted for preventing the patient from inadvertently activating the at least one bolus delivery button.

In one implementation, the therapeutic fluid dispensing mechanism comprises a pump. In another implementation, the therapeutic fluid delivery device comprises two or more bolus delivery buttons and the inadvertent initiation prevention mechanism prevents the controller from initiating the delivery of the therapeutic fluid into the body of the patient unless the patient activates the two or more bolus delivery buttons substantially simultaneously. In another implementation, the device comprises two or more bolus delivery buttons and the inadvertent initiation prevention mechanism prevents the controller from initiating the delivery of the therapeutic fluid into the body of the patient unless the patient activates the two or more bolus delivery buttons according to an activation sequence.

The controller can further be adapted to interrupt the delivery of the therapeutic fluid into the body of the patient in response to a command received from the patient. In one implementation, the patient can send the command by using the at least one bolus delivery button. In another example, a notification component can be provided which is adapted for sending a notification to the patient corresponding to the delivery of the therapeutic fluid. For example, the notification can be at least one of the visual notification, audio notification and tactile notification.

In one implementation, the at least one bolus delivery button comprises a slidable portion. In another implementation, the at least one bolus delivery button comprises a rotatable element. In yet another implementation, a first of the at least one bolus delivery buttons is positioned on a first side of the therapeutic fluid delivery device and a second of the at least one bolus delivery buttons is positioned on a second side of the therapeutic fluid delivery device.

The fluid delivery device, for example, can comprise three units: a dispensing patch unit (also referred to as "dispensing unit" or "dispensing patch"), a skin adherable cradle unit and a remote control unit. The dispensing patch unit may employ different dispensing mechanisms, such as a syringe-type reservoir with a propelling plunger or a peristaltic positive displacement mechanism, and the like. After attaching the cradle unit to the skin, a cannula is inserted into the subcutaneous compartment through a dedicated passage ("well") in the cradle unit. The dispensing patch unit can then be connected to the cradle unit. The dispensing patch unit's outlet port is provided with a short connecting lumen which pierces a self-sealable rubber septum that seals the well. The connecting lumen allows fluid communication between the dispensing patch unit and the cannula. The dispensing patch unit can be connected to and disconnected from the skin adherable cradle unit upon patient discretion. In one preferred embodiment, a remote control unit communicates with the dispensing patch unit and allows programming of therapeutic fluid delivery, and allows user input and data acquisition. In another preferred embodiment, bolus delivery programming is carried out manually by manually operating bolus switch(es)/button(s) ("buttons") located on the dispensing patch unit, which then electronically control the dispensing patch unit. In yet another preferred embodiment, bolus delivery programming can be carried out either by a remote control unit or manually by electronically operating bolus button/s located on the dispensing patch unit.

In one preferred embodiment, the dispensing patch unit comprises two parts: a reusable part and a disposable part. The disposable part can contain a reservoir and an outlet port, and the reusable part can contain electronics, at least a portion of a fluid dispensing mechanism and bolus button/s for manually initiating electronically operated bolus dosage delivery in case the remote control unit is not at hand, lost, nonfunctional, or in case the user wishes to initiate bolus dosage delivery in a discreet manner without using the remote control unit.

In a preferred embodiment, the reusable part of the dispensing patch unit is provided with two buttons which are located oppositely from each other on the lateral walls of the reusable part's housing. In order to initiate bolus dosage delivery, the patient is required to press both buttons simultaneously, thus ensuring that bolus delivery cannot be initiated unintentionally. The bolus buttons, according to one preferred embodiment, are electronic switches, i.e. each button serves as a contact switch together with a portion of the printed circuit board (PCB) which is coated with a conductive material. When the patient presses the two buttons simultaneously, both switches are in an "ON" state, thus a signal is sent to the central processing unit (CPU) to activate the motor such that a bolus dose will be delivered. Alternatively, the buttons may be set up such that pressing both buttons would place the switches in an "OFF" state (i.e., disconnecting one or more "status" circuits within the unit). Such embodiments may or may not include the ability to supply basal dosages to the patient.

A portable therapeutic fluid delivery device capable of supplying both basal and bolus doses of a therapeutic fluid can also be provided. For example, it can include a dispensing unit comprising a reservoir for containing the therapeutic fluid, a pump for enabling fluid to flow out of the reservoir and through a delivery tube to a patient, a controller for controlling operation of the pump and a plurality of buttons capable of being depressed by a patient/user, wherein depressing the buttons is sensed by the controller to enable a bolus dose to be delivered to the patient.

In the above noted embodiment, the controller enables delivery of the bolus dose only upon the plurality of buttons being simultaneously or sequentially pressed, and if the controller is setup to enable delivery of the bolus dose upon sequential pressing of the buttons, such setup may include a predetermined order of sensed sequential pressing of the buttons. Such depressing of the buttons may establish a circuit in the device which is sensed by the controller.

The controller of the portable therapeutic fluid delivery device may comprise a processor capable of being programmed to delivery a specific, predetermined amount of the therapeutic fluid per bolus dose, which can be modified by the patient/user (or healthcare professional).

A method for delivering a therapeutic fluid using a portable therapeutic fluid delivery device is also described. In some implementations the method may include providing a therapeutic fluid delivery device (according to any one of the above-noted embodiments), and depressing the plurality of buttons either simultaneously or sequentially which is sensed by the controller to deliver a bolus dose of the therapeutic fluid.

For example, electronic bolus buttons can have the following advantages:
  The bolus dosage can be delivered from the same reservoir as the basal dosage. Thus, no additional space-consuming intermediate reservoirs are required.
  No additional mechanical components (e.g. springs, tubes, etc.) are required. Thus, the miniature size and cost-effectiveness of the dispensing patch are maintained.
  The user can program the amount of therapeutic fluid (e.g. insulin) to be delivered in a single pressing of the button/s. For example, 0.5 unit for children, 1 unit for adults. Alternatively, the CPU can be pre-programmed such that different amounts of fluid will be delivered depending on the length of time that the button/s is/are maintained pressed. For example, 0.5 unit when the button/s is/are maintained pressed for 2 seconds, 0.75 units when the button/s is/are maintained pressed for 3 seconds, etc. It should be noted, however, that the maximum programmable amount for a single pressing of the button/s should be limited by the dispensing patch's software to prevent drug overdose.
  The user can press the button/s several times consecutively without wait. In some embodiments a minimal waiting period between two consecutive pressings may be required for system adjustment (e.g. 1 second). The total amount of fluid to be delivered in one bolus dosage (i.e. as a result of two or more consecutive pressings of the button/s) should also be limited by the dispensing patch's software in order to prevent a drug overdose.
  The CPU can be pre-programmed such that after initiating the bolus delivery the user can interrupt the fluid delivery by pressing the button/s again. Interrupting the fluid delivery may require, for example, pressing the button/s for a prolonged period (e.g. longer than 5 seconds).
  The CPU can be pre-programmed such that pressing one button initiates bolus delivery, whereas pressing a second button interrupts the bolus delivery.
  The CPU can be pre-programmed to give the user appropriate indications via the notification component, for example in the following cases:
    Proper pressing of the button/s which results in bolus dosage delivery.
    Faulty pressing of the button/s which does not result in bolus dosage delivery. Examples of faulty pressing of the button/s could be pressing only one button when two or more buttons are employed, keeping one or more buttons pressed for a period of time which exceeds a pre-programmed period of time (e.g. 1 minute), etc.
    Reaching the pre-programmed limit of the fluid amount which can be delivered in one bolus dosage.

In some implementation a device that contains a skin adherable infusion unit (also referred to as "dispensing patch unit", "dispensing unit" or "dispensing patch") that employs means for manually initiating bolus dosage delivery can be provided. In some implementations, a dispensing patch unit that employs bolus dosage delivery means that is manually initiated and electronically operated can also be provided. For example, a device can contain a dispensing patch that is programmable by a remote control unit and in addition employs means for bolus dosage delivery that is manually initiated and electronically operated. The dispensing patch, in some implementations, can be attached to the body at any desired location, and employ means for bolus dosage delivery that is manually initiated and electronically operated.

In some implementations, a dispensing patch can have a thin profile (i.e. it can be discreet), has no tubing, and employs means for bolus dosage delivery that is manually initiated and electronically operated. A dispensing patch can also comprise a reusable part and a disposable part. The reusable part can contain electronics, fluid dispensing mechanism, and means for bolus dosage delivery that is manually initiated and electronically operated, and the disposable part contains a reservoir and outlet port.

A dispensing patch can employ means for bolus dosage delivery that can be manually initiated and electronically operated, and that is safe and avoid unintentional pressing and consequently unwanted bolus doses. A dispensing patch can also employ means for bolus dosage delivery that is manually initiated and electronically operated, and that is simple and cost-effective.

BRIEF DESCRIPTION OF THE DRAWINGS

FIGS. 1a-c provide some examples of a single-part dispensing patch unit, a two-part dispensing patch unit and a remote control unit.

FIGS. 2a-c provide some examples of a dispensing patch unit directly adhered to a patient's skin.

FIGS. 3a-c show exemplary connection of a dispensing patch unit to a cradle unit.

FIGS. 5a-b provide some examples of the dispensing patch unit and the cradle unit before and after connection.

FIGS. 9a-b provide some examples of a dispensing patch unit which employs a syringe-type pumping mechanism with manual bolus buttons.

FIGS. 14a-b show the exemplary bolus button being pressed.

FIG. 17 shows an exemplary reusable part provided with manual bolus buttons, the operation of which is based on capacitive sensing.

DETAILED DESCRIPTION OF THE INVENTION

Figure 4A:
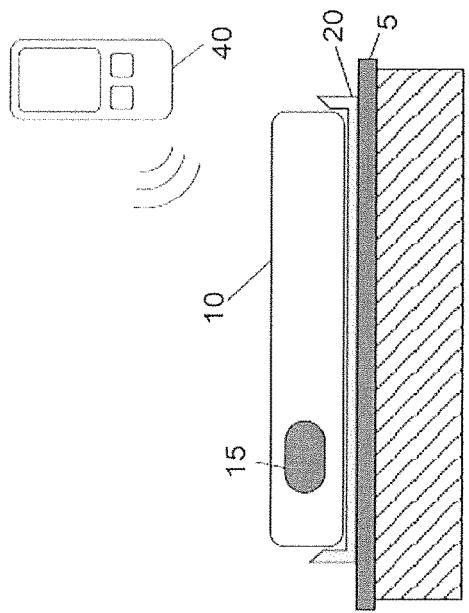
FIGS. 4a-b provide some examples of a single-part dispensing patch unit, a two-part dispensing patch unit, a remote control unit and a cradle unit.

FIG. 1a shows a fluid delivery device (1) comprising a dispensing patch unit (10). The fluid delivery device (1) may also comprise a remote control unit (40). The dispensing patch unit (10) may be composed of a single part (FIG. 1b) or two parts (FIG. 1c), e.g. a reusable part (100) and a disposable part (200).

FIGS. 2a-c show an example of direct adherence of a dispensing patch unit (10) to the patient's skin (5). FIG. 2a shows the peeling of an adhesive protective sheet (101) from the dispensing patch unit (10). FIG. 2b shows the adherence of the dispensing patch unit (10) to the patient's skin (5). FIG. 2c shows the dispensing patch unit (10) adhered and ready for operation.

In another preferred embodiment shown in FIGS. 3a-c the device also employs a cradle unit (20), which can be adhered first to the patient's skin (5) and the dispensing patch unit (10) can then be connected to and disconnected from the cradle unit (20) upon patient discretion. The device employing the cradle unit is described in our U.S. patent application No. 60/876,679, incorporated herein by reference in its entirety.

FIG. 3a shows the cradle unit (20) adhered to the patient's skin (5). FIG. 3b shows the connection of the dispensing patch unit (10) to the adhered cradle unit (20). FIG. 3c shows the dispensing patch unit (10) connected to the cradle unit (20) and ready for operation.

FIG. 4a shows the fluid delivery device comprising a single-part dispensing patch unit (10), cradle unit (20) and remote control unit (40). The dispensing patch unit (10) is connected to the cradle unit (20) after adherence of the cradle unit (20) to the patient's skin (5). In some implementations, infusion programming can be carried out either by a remote control unit (40) having a bidirectional communication link (for example) with the transceiver provided in the dispensing patch unit (10) or by one or more manual bolus buttons (15) provided in the dispensing patch unit (10). The employment of manual bolus button/s in a skin adherable dispensing patch unit (10) is highly advantageous since it allows the delivery of bolus dosages of therapeutic fluid (e.g. insulin) without requiring the use of the remote control unit (40). Such manual operation of the infusion pump may be required, for example, if the remote control unit is nonfunctional, lost or not at hand, or if the patient wishes to initiate bolus delivery discreetly. The bolus button/s, in some implementations, can be electronic, as will be explained in detail below.

In some implementations the button/s can be further used to interrupt the fluid delivery. For example, after pressing the button/s to initiate the fluid delivery, the user can interrupt the fluid delivery by pressing the button/s again. Interrupting the fluid delivery may require, for example, pressing the button/s for a prolonged period (e.g. longer than 5 seconds). In some implementations the setup may be such that pressing one button initiates the fluid delivery, whereas pressing a second button interrupts the fluid delivery.

Figure 4B:
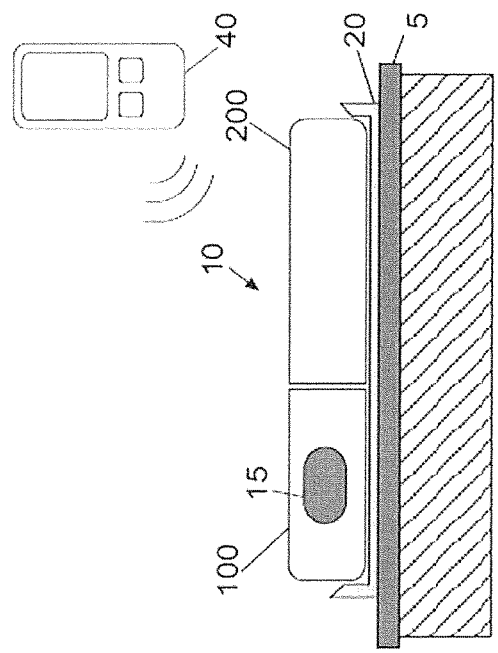

FIG. 4b shows the fluid delivery device comprising a two-part dispensing patch unit (10), a cradle unit (20) and a remote control unit (40). In this embodiment the manual bolus button/s (15) are located on the reusable part (100) of the dispensing patch unit (10).

FIG. 5a shows an example of a two-part dispensing patch unit (10) and a cradle unit (20) after a cannula (330) has been inserted into the subcutaneous tissue (4) and before connection of the dispensing patch unit (10) to the cradle unit (20). The dispensing patch unit (10) contains, inter alia, a fluid reservoir (220), outlet port (213) and connecting lumen (214) that maintains fluid communication between the reservoir (220) and the cannula (330).

FIG. 5b shows the connection of the dispensing patch unit (10) to the cradle unit (20). Upon connection of the two units, the connecting lumen (214) pierces a septum (311) sealing the cradle unit's (20) dedicated fluid passage ("well") (310), thus allowing fluid delivery via the cannula (330) to the subcutaneous tissue (4). The outlet port (213) allows repetitive connection and disconnection of the dispensing patch unit (10) to and from the cradle unit (20).

Figure 6B:
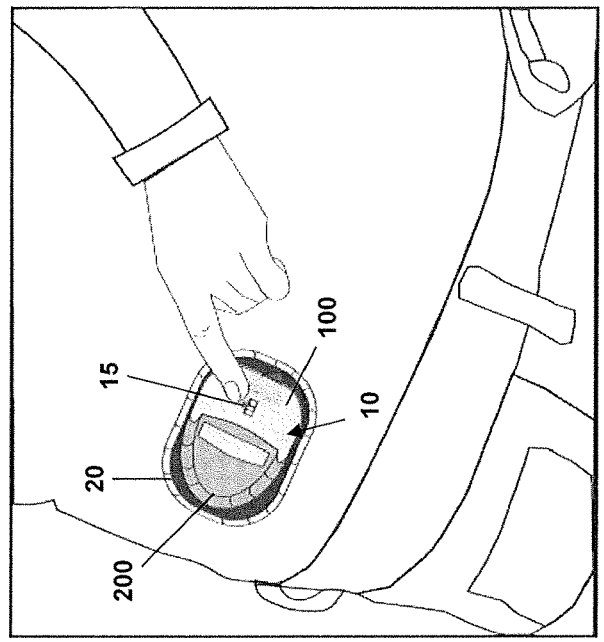
FIGS. 6a-b provide some examples of a dispensing patch unit with a single bolus button.
Figure 6A:
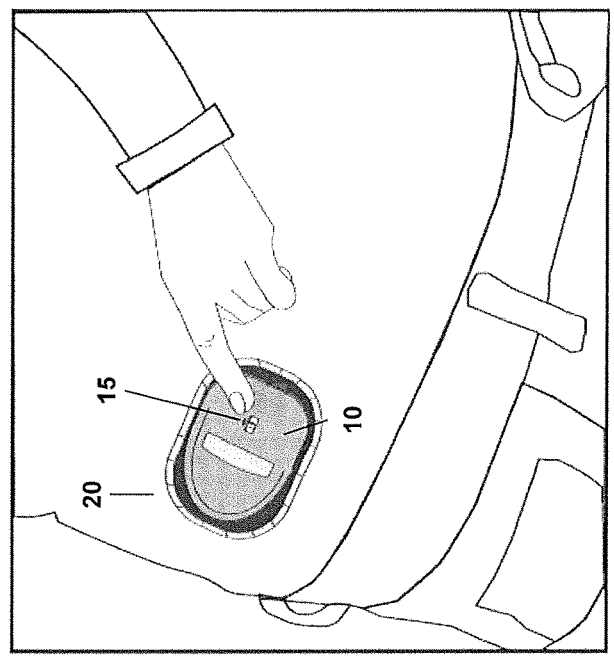

FIGS. 6a-b show a user manually operating a single-part dispensing patch unit (10) (FIG. 6a), and a two-part dispensing patch unit (10) (FIG. 6b), by pressing a single bolus button (15) provided on the dispensing patch unit (10). In case a two-part dispensing patch unit (10) is used, the bolus button (15) is preferable located on the reusable part (100).

Figure 7B:
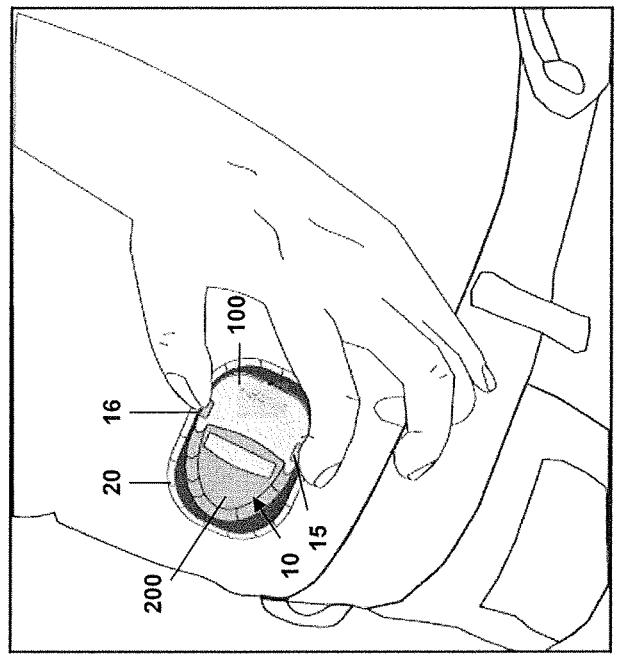
FIGS. 7a-b provide some examples of a dispensing patch unit with two bolus buttons.
Figure 7A:
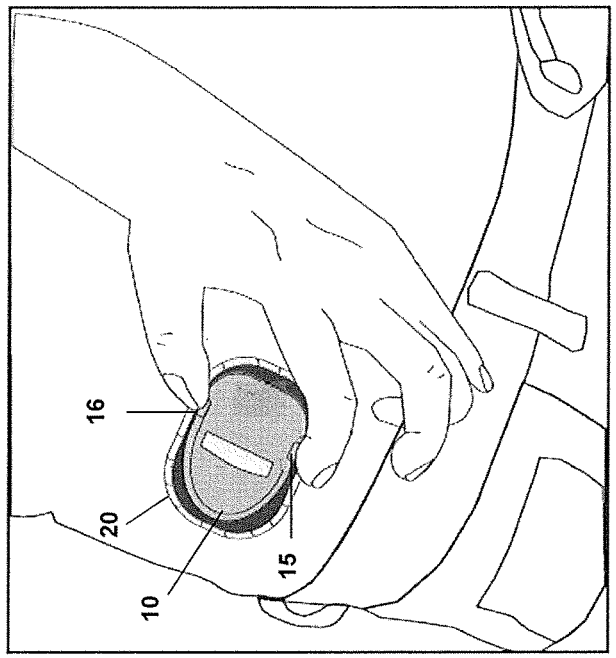

FIGS. 7a-b show a user manually operating a single-part dispensing patch unit (10) (FIG. 7a), and a two-part dispensing patch unit (10) (FIG. 7b), by simultaneously pressing two bolus buttons (15, 16) provided on the dispensing patch unit (10). In case a two-part dispensing patch unit (10) is used, the bolus buttons (15, 16) are preferable located on the reusable part (100).

It will be noted that the dispensing patch unit may otherwise be provided with more than two bolus buttons. It will also be noted that the location of the button/s on the dispensing patch unit is not limited to any specific location, and FIGS. 6-7 demonstrate only one example of the various possible locations of the bolus button/s on the dispensing patch unit.

The dispensing patch unit (10) may employ different dispensing mechanisms (e.g. syringe-type reservoir with a propelling plunger, peristaltic pump, or other mechanisms which can be used to dispense fluid from a corresponding reservoir), and various types of driving mechanisms (e.g.

DC or stepper motors, SMA actuator, etc.). Manual bolus buttons, in some implementations, may be employed in any one of the different types of a dispensing patch unit.

Figure 8A:
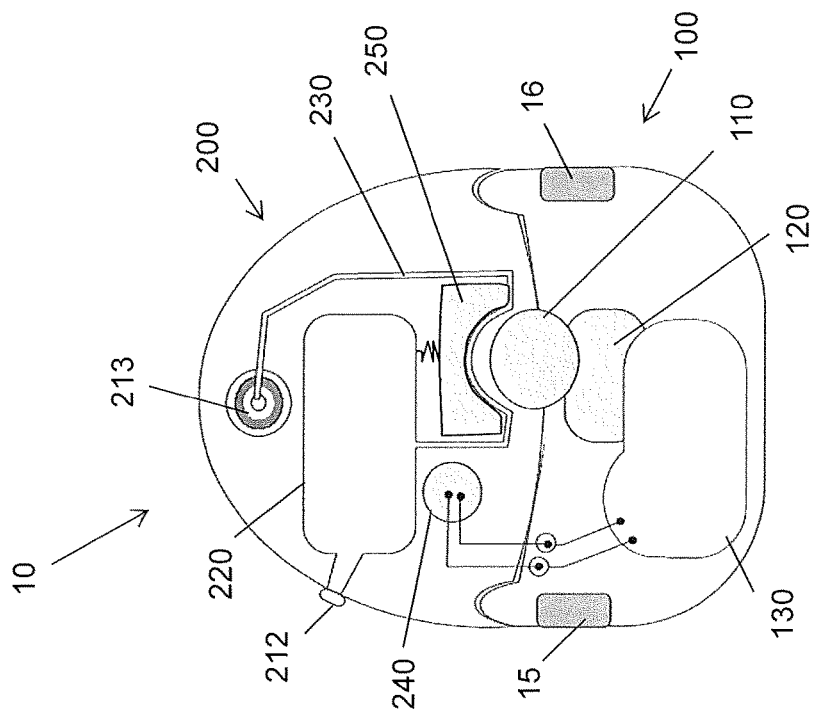
FIGS. 8a-b provide some examples of a dispensing patch unit which employs a peristaltic pumping mechanism with manual bolus buttons.
Figure 8B:
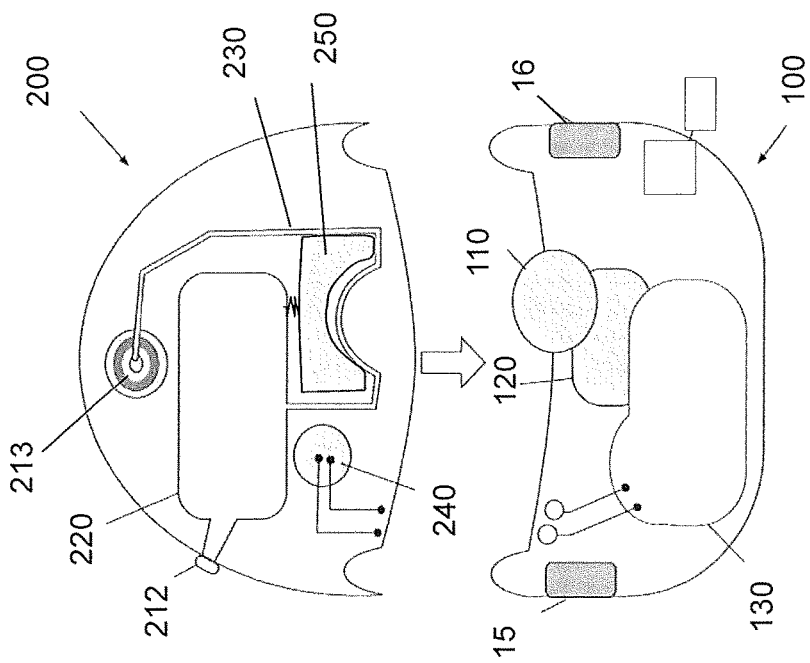

FIGS. 8a-b show an example of a two-part dispensing patch unit (10) which employs a peristaltic pumping mechanism and is provided with bolus buttons (15, 16). FIG. 8a shows the reusable part (100) and the disposable part (200) prior to connection. Each part is contained in a separate housing. The reusable part (100) comprises a rotary wheel (110) provided with rollers (not shown), driving mechanism (120), printed circuit board (PCB) (130) with electronic components and bolus buttons (15, 16). The location of the bolus buttons (15, 16) on the reusable part (100), as well as the number of bolus buttons, may vary. The disposable part (200) comprises a reservoir (220) provided with an inlet port (212) for filling, delivery tube (230), energy supply means (240) which can be one or more batteries, outlet port (213) and stator (250). Fluid dispensing is possible after connecting the reusable part (100) with the disposable part (200). Rotation of the rotary wheel (110) and pressing of rollers against the stator (250) periodically positively displaces fluid from the reservoir (220) into the delivery tube (230) by virtue of a peristaltic motion. The fluid is then delivered via a cannula into the subcutaneous compartment. This arrangement is described in co-owned/co-pending U.S. patent application Ser. No. 11/397,115 and International Patent Application No. PCT/IL06/001276, disclosers of which are incorporated herein by reference in their entireties.

FIG. 8b shows the dispensing patch unit (10) after connection of the reusable (100) and disposable (200) parts.

FIGS. 9a-b show an example of a two-part dispensing patch unit (10) which employs a syringe-type pumping mechanism and is provided with manual bolus buttons (15, 16).

FIG. 9a shows the reusable part (100) and the disposable part (200) prior to connection. Each part is contained in a separate housing. In this embodiment, the plunger (210) is located in the disposable part (200). The disposable part also comprises a reservoir (220), energy supply means (240) and outlet port (213). The reusable part (100) comprises a driving mechanism (120), PCB (130) with electronic components and manual bolus buttons (15, 16). The location of the bolus buttons (15, 16) on the reusable part (100), as well as the number of bolus buttons, may vary.

FIG. 9b shows the connection of the reusable (100) and disposable (200) parts, including the engagement of the plunger rod (211) with the driving mechanism (120) and the establishment of electrical connection between the energy supply means (240) and the PCB (130). This arrangement was described in co-owned/co-pending International Patent Application No. PCT/IL08/000641, filed May 11, 2008, claiming priority to U.S. Provisional Patent Application No. 60/928,815, entitled "A positive displacement pump", filed May 11, 2007, the disclosure of which is incorporated herein by reference in its entirety.

FIGS. 10-16 show a preferred embodiment of a two-part dispensing patch unit which employs a peristaltic pumping mechanism and includes bolus buttons for enabling the device to dispense a bolus dose without the use of a remote control unit. It will be noted that all bolus buttons' configurations and/or mechanisms described below may also be implemented in a single-part dispensing patch unit and in a dispensing patch unit employing a non-peristaltic pumping mechanism, e.g. a syringe-type mechanism.

Figure 10B:
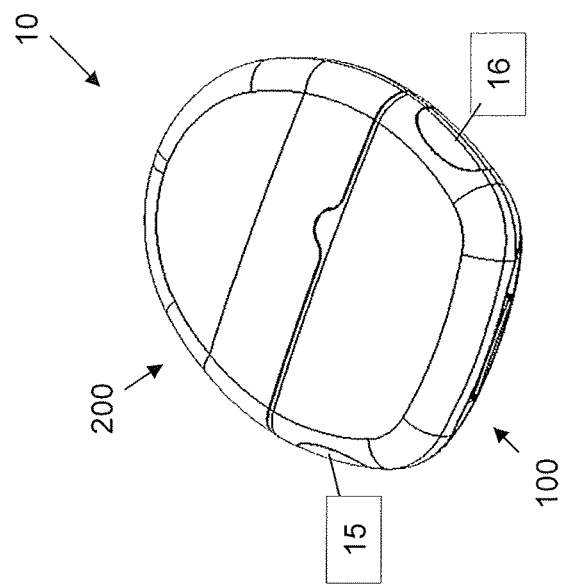
FIGS. 10a-b provide some examples of a dispensing patch unit with manual bolus buttons.
Figure 10A:
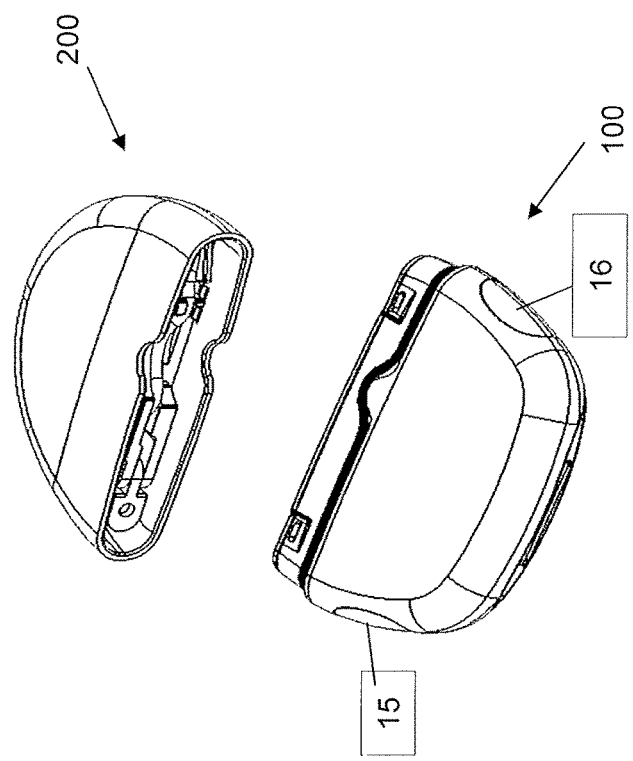

FIG. 10a shows a reusable part (100) and a disposable part (200) contained in separate housings. In this embodiment two bolus buttons (15, 16) are provided for safety reasons, as will be explained below. The bolus buttons (15, 16) in this embodiment are located on the reusable part (100), and they are preferably fabricated using an overmolding process, i.e. the housing of the reusable part (100) is pre-molded having two dedicated apertures, and it is then placed in a second mold so that the bolus buttons (15, 16) are fabricated inside the dedicated apertures. This process assures that the reusable part, and consequently the dispensing patch unit, remains water-tight. The bolus buttons (15, 16) are preferably fabricated from a resilient material, e.g. rubber.

FIG. 10b shows the dispensing patch unit (10) after connection of the two parts.

Figure 11:
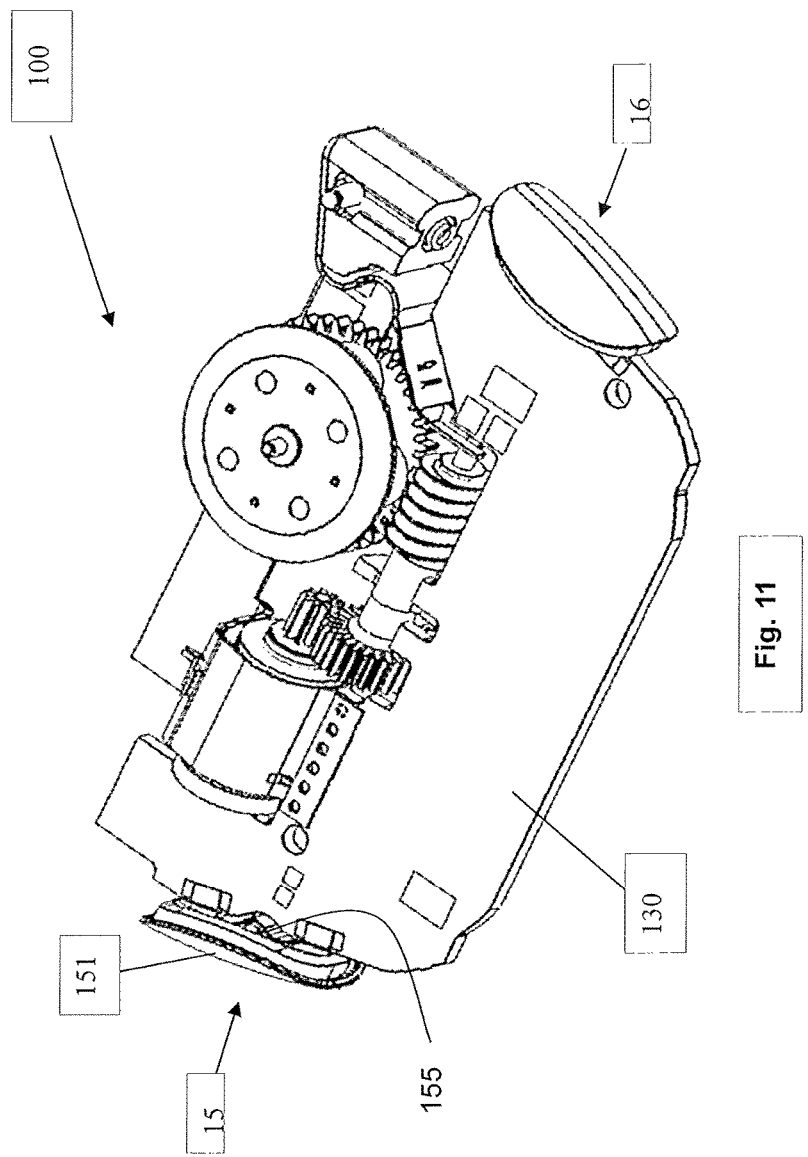
FIG. 11 provides some examples of a reusable part with manual bolus buttons, the operation of which is based on electronic switches.

FIG. 11 shows the reusable part (100) without its housing. In this embodiment, each bolus button (e.g. the button designated by numeral 15) may include a button portion (151) which is accessible to the patient and is preferably fabricated from a resilient material, e.g. rubber, and button contacts, i.e. a metal strip (155) which is soldered to the PCB (130) and serves as a contact switch together with a portion of the PCB (130), as will be explained below.

Figure 12B:
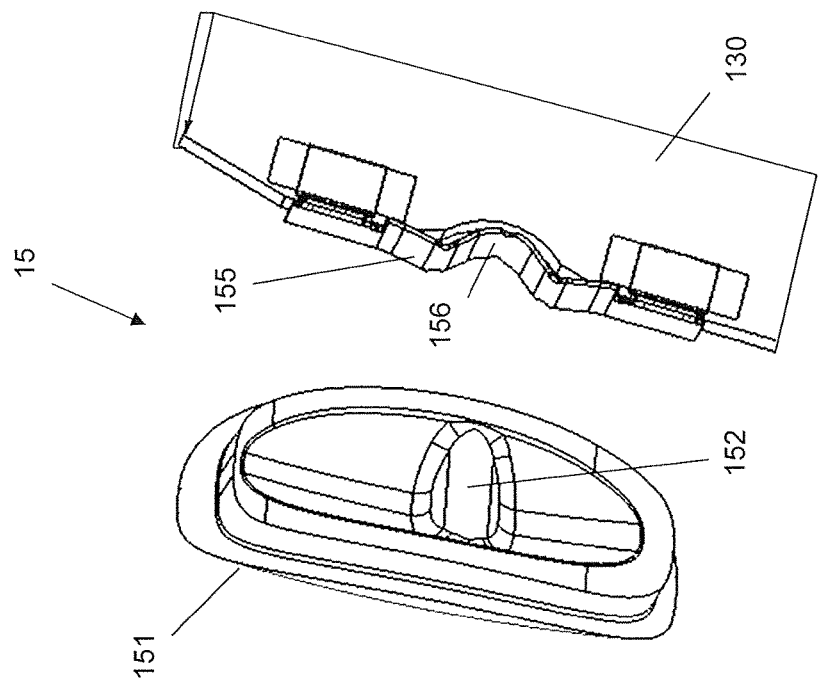
FIGS. 12a-b show side and perspective views of the two parts of the exemplary bolus button.
Figure 12A:
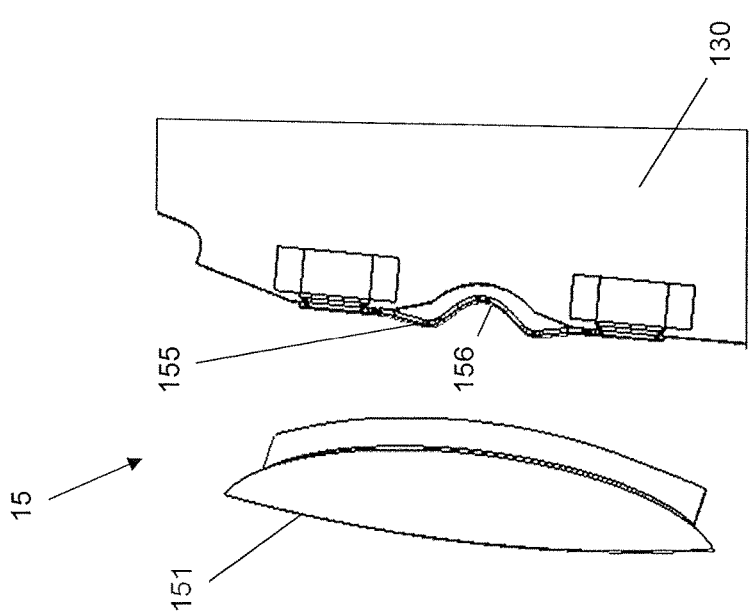

FIGS. 12a-b show side and perspective views (respectively) of the two parts of the bolus button (15); the button portion (151) and the metal strip (155), which is soldered to the PCB (130). The button portion (151) has a protrusion (152) on its inwardly facing side, which is designed to fit into the concave portion (156) of the metal strip (155). It will be noted that the two bolus buttons in this embodiment are identical, therefore the above description, as well as all further descriptions relating to one of the buttons, applies to both bolus buttons equally.

Figure 13B:
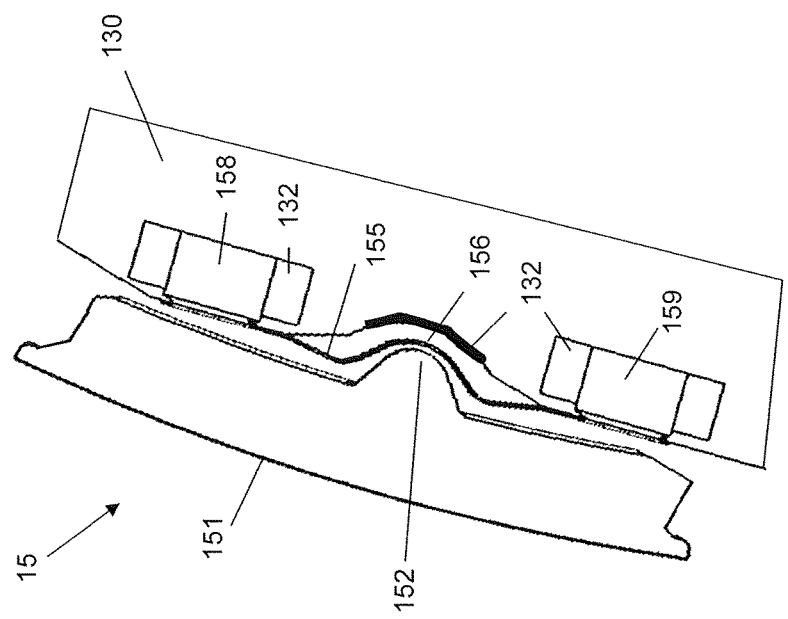
FIGS. 13a-b show perspective and cross-sectional views of the exemplary bolus button when it is not pressed.
Figure 13A:
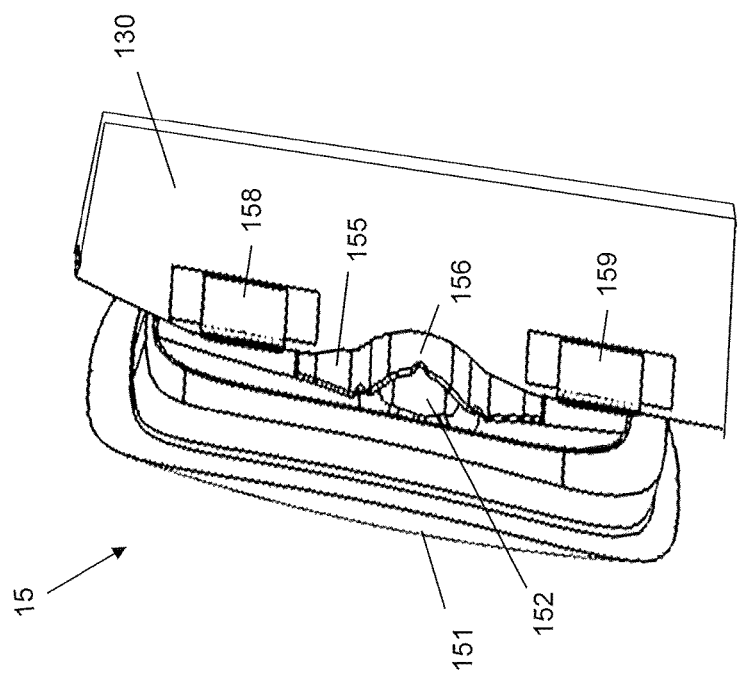

FIGS. 13a-b show perspective and cross-sectional views (respectively) of the bolus button (15) in an initial position (prior to being depressed). It can be seen that when not pressed, the protrusion (152) on the inwardly facing side of the button portion (151) is positioned in close proximity to the metal strip (155) on its concave portion (156).

In this embodiment, the PCB (130) is provided with conductive pads (e.g. fabricated of gold or other conductive material) (132) at the two soldering points (158, 159) of the metal strip (155) and on a portion of the lateral face of the PCB (130) which is located between said soldering points (158, 159). The conductive pads (132) form a contact switch together with the button's metal strip (155).

FIGS. 14a-b shows a user pressing the bolus button (15). When the bolus button (15) is pressed, the button portion (151) curves inwardly. As a result, the protrusion (152) on the button portion's inwardly facing side comes in contact with the metal strip (155) and pushes it against the conductive pad (132) on the lateral face of the PCB (130). When contact is established between the metal strip (155) and the conductive pad (132), a short circuit occurs, and the switch is in an "ON" state.

In order to prevent inadvertent initiation of bolus dosage delivery, two buttons are provided. Thus, in some implementations, only simultaneous pressing of the two buttons (both switches are in an "ON" state) will initiate bolus dosage delivery (or sequential depressing of the buttons). It will be noted that the two bolus buttons are preferably positioned opposite from each other, e.g. on opposite lateral walls of the dispensing patch unit's reusable part, in order to prevent unintentional simultaneous pressing of the buttons.

An arrangement of one button with a locking mechanism (preferably automatic locking), in which the locking mechanism must be held in an unlocked position to press the button, and other similar embodiments, can also be used in some implementations (see, for example, FIGS. 19-22 and accompanying description).

Figure 15:
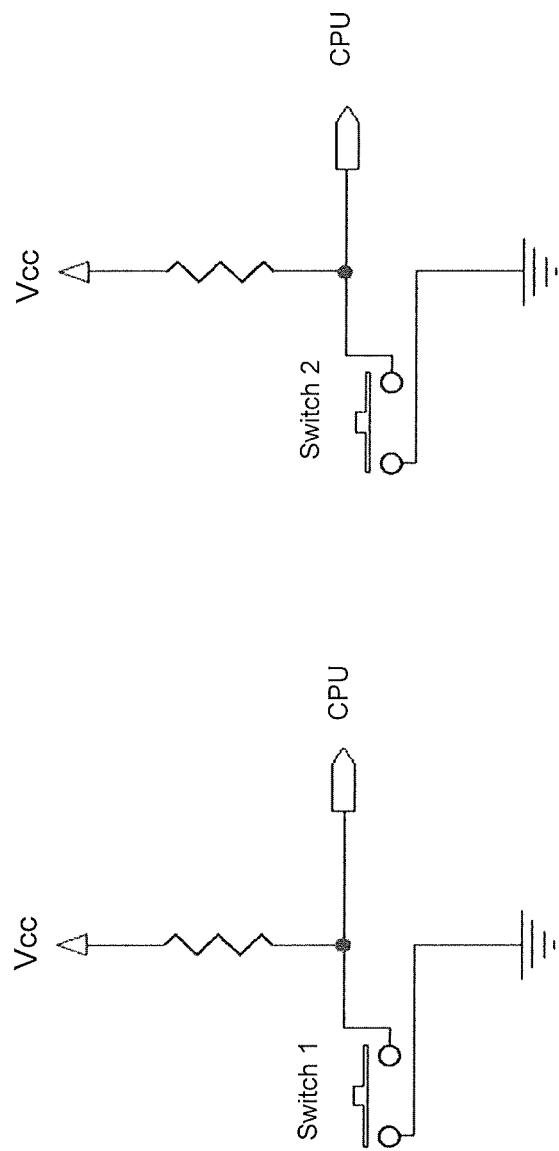
FIG. 15 shows the electronic circuits of the two contact switches corresponding to the two exemplary bolus buttons.

FIG. 15 shows the electronic circuits of the two contact switches corresponding to the two bolus buttons (15, 16). Both circuits are connected to the ground on one end and to a power source and the CPU's inlet port on the other end.

Figure 16:
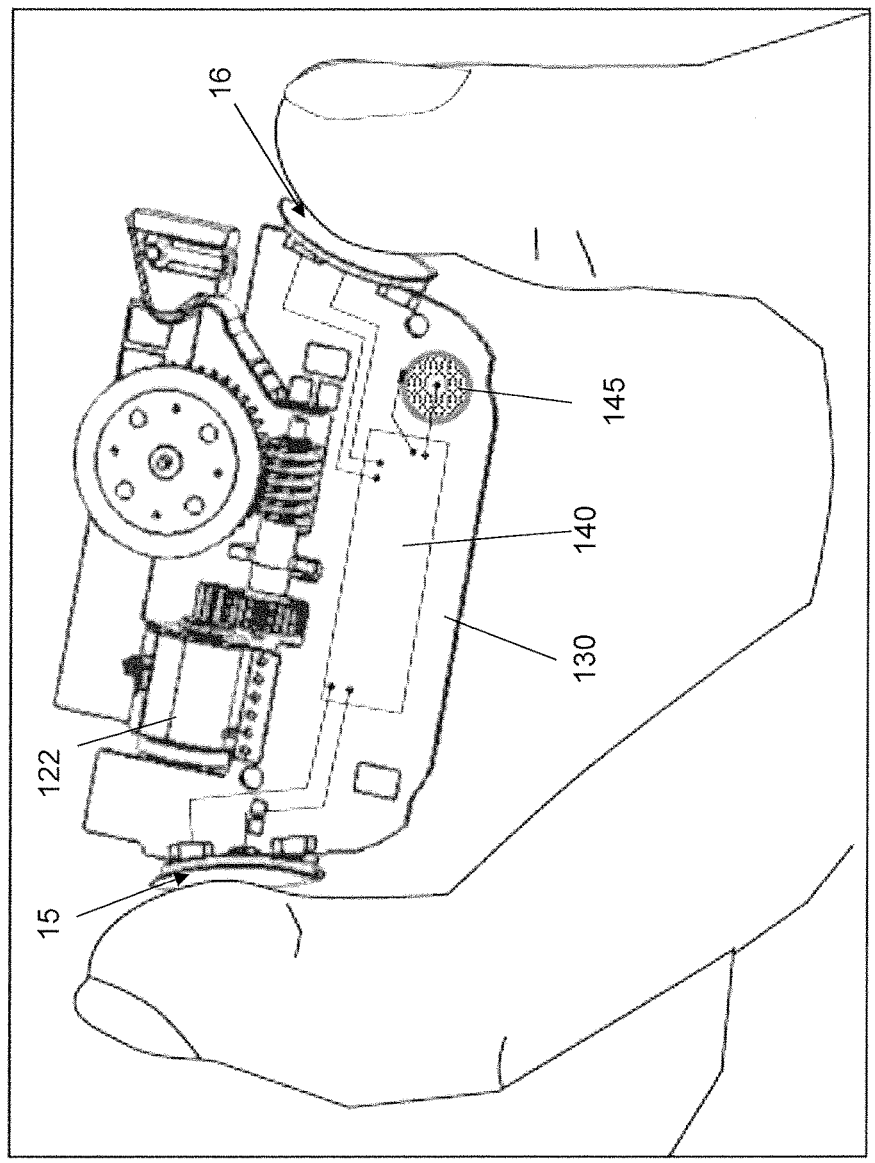
FIG. 16 shows two exemplary bolus buttons being pressed simultaneously.

FIG. 16 shows a user simultaneously pressing the two bolus buttons (15, 16). Both switches are now in an "ON" state, thus a signal is sent to the CPU (140) to activate the motor (122) such that a bolus dose of therapeutic fluid (e.g. insulin) is delivered. The CPU (140) in this embodiment is programmed to execute bolus delivery only when both switches are in an "ON" state, i.e. a logic command of (Switch 1 AND Switch 2). If only one switch is in an "ON" state (i.e. only one button is being properly pressed), a bolus dosage will not be delivered. The CPU (140) can also indicate to the patient, via the notification component (145), if bolus delivery has been initiated. The CPU (140) may also be programmed to alert the patient via the notification component (145) if bolus delivery has not been initiated due to faulty pressing of the bolus buttons (e.g. only one button is being properly pressed). The notification component (145) may be audible (e.g. a buzzer), visible (e.g. flashing lights) or tactile (e.g. vibrator).

An alternative embodiment may include a commercially available tactile switch (e.g. tact switches manufactured by Alps Electric Co., Ltd., Japan), which is soldered to the PCB and connected to the CPU, instead of providing a dedicated metal strip in each bolus button, thus simplifying the manufacturing process of the buttons. If a commercially available tactile switch is used, then when the user presses the button portion, the protrusion on its inwardly facing side is pushed against the tactile switch, thus turning it on. When the user presses both buttons simultaneously, both tactile switches are in an "ON" state, thus a signal is sent to the CPU to activate the motor such that a bolus dose of therapeutic fluid (e.g. insulin) is delivered.

It will be noted, that the buttons may alternatively be set up such that pressing a button would place the switch in an "OFF" state (i.e., disconnecting one or more "status" circuits within the unit), and bolus delivery would be initiated only when both switches are in an "OFF" state (or when the buttons are sequentially pressed).

FIGS. 17-18 show another embodiment of electronic bolus buttons. In this embodiment the operation of the buttons is based on sensing capacitance changes, as will be explained below.

FIG. 17 shows an embodiment of a reusable part (100) provided with two bolus buttons (17, 18). In this embodiment each bolus button (e.g. the button designated by numeral 17) consists of a button portion (171), which is accessible to the patient and is preferably configured as a thin sheet fabricated from non-conductive material (e.g. rubber, plastic), and a capacitor which is comprised of two conductive pads (175, 176) provided on the PCB (130). The conductive pads (175, 176) may be parallel to each other or they may be configured as two concentric annuli pads, or as one circular pad surrounded by a second pad having a uniform gap between the two pads, etc. The buttons are provided with at least one commercially available sensor chip (178) (e.g. a sensor chip manufactured by Omron Electronic Components Europe B. V., The Netherlands), which charges the capacitors.

Accordingly, when the user presses the button portion (171) against the conductive pads (175, 176), the user's finger, which has conductive properties, adds conductive surface area to the conductive pads (175, 176), thus increasing the capacitor's capacitance. The sensor chip (178) measures the capacitor's capacitance, and either signals the CPU (140) when the button (17) is pressed, according to a preprogrammed capacitance threshold (or derivative voltage threshold, etc.), or transmits to the CPU (140) the measured capacitance, and the CPU (140) determines if the button (17) is pressed or not according to a preprogrammed capacitance threshold (or derivative voltage threshold, etc.). For safety reasons, the threshold should be determined such that the capacitance (or voltage, etc.) threshold will be reached only when the button (17) is completely pressed, i.e., when the button portion (171) touches the conductive pads (175, 176). The CPU (140) can be programmed to execute bolus delivery only when both buttons are being pressed and to indicate to the patient, via the notification component (145), whether a bolus delivery has been initiated or not.

Figure 18B:
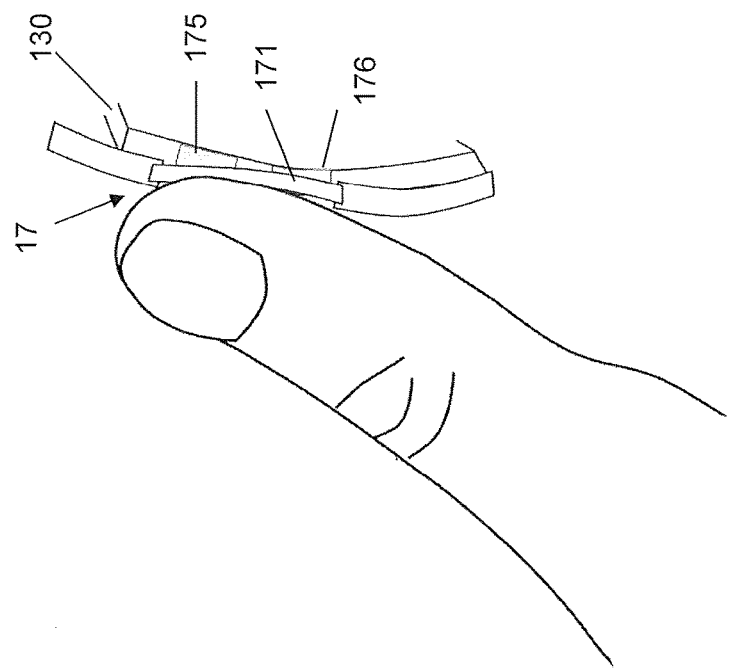
FIGS. 18a-b show perspective views of the exemplary bolus button being pressed.
Figure 18A:
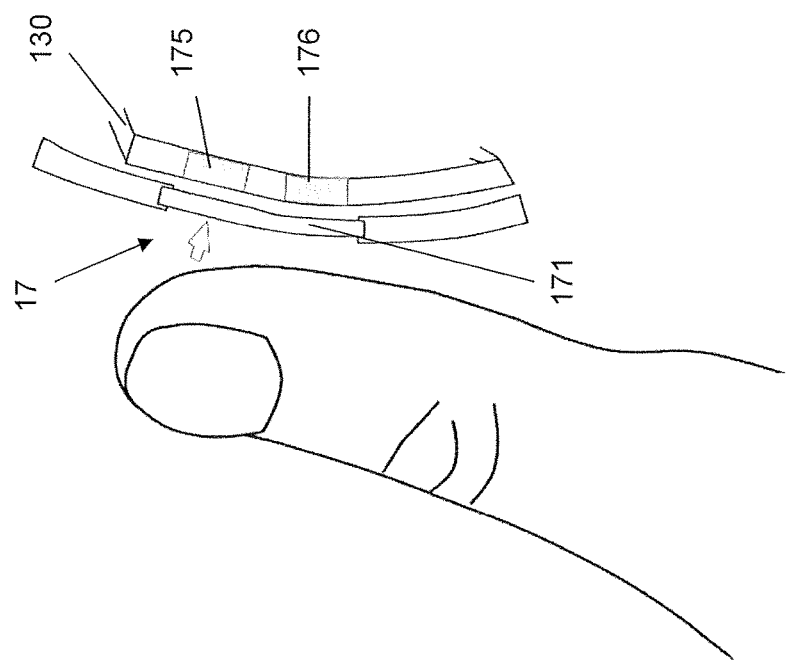

FIGS. 18a-b show perspective views of one of the bolus buttons (17) being pressed. The bolus button (17) comprises two conductive pads (175, 176) provided on the PCB (130), and a button portion (171) which is configured as a thin sheet fabricated from non-conductive material, e.g. rubber, plastic, etc.

In some implementations, the bolus buttons can be using the "Hall Effect". For example, each button can comprise a button portion which is located on the reusable part's housing (in case of a two-part dispensing patch unit), and is preferably fabricated from a resilient material, e.g. rubber, using the over-molding process. At least one magnet can either be embedded in the button portion or protrudes from it, in the button portion's inwardly facing side. In addition, each button is provided with a Hall Effect sensor, which is attached to the PCB in proximity to the button portion, and is connected to the CPU either directly or via another electronic component, e.g. a comparator. When the button is not being pressed, the electrical signal transmitted by the Hall Effect sensor remains constant. When the button is being pressed, the magnet is moved towards the dedicated Hall Effect sensor, thus exposing the sensor to the magnet's magnetic field and causing the electrical signal transmitted by the Hall Effect sensor to peak. The CPU can be programmed to execute bolus delivery only when both buttons are being pressed, i.e., when the electrical signals transmitted by both Hall Effect sensors peak simultaneously. The CPU is also preferably programmed to indicate to the patient, via the notification component, whether bolus delivery has been initiated or not.

FIGS. 19-22 show some implementations, in which the dispensing patch unit is provided with a single bolus button. In order to prevent unintentional pressing of the button, safety mechanisms are employed, as will be explained further. The embodiments described below can be employed in either a single-part dispensing patch unit or a two-part dispensing patch unit.

Figure 19:
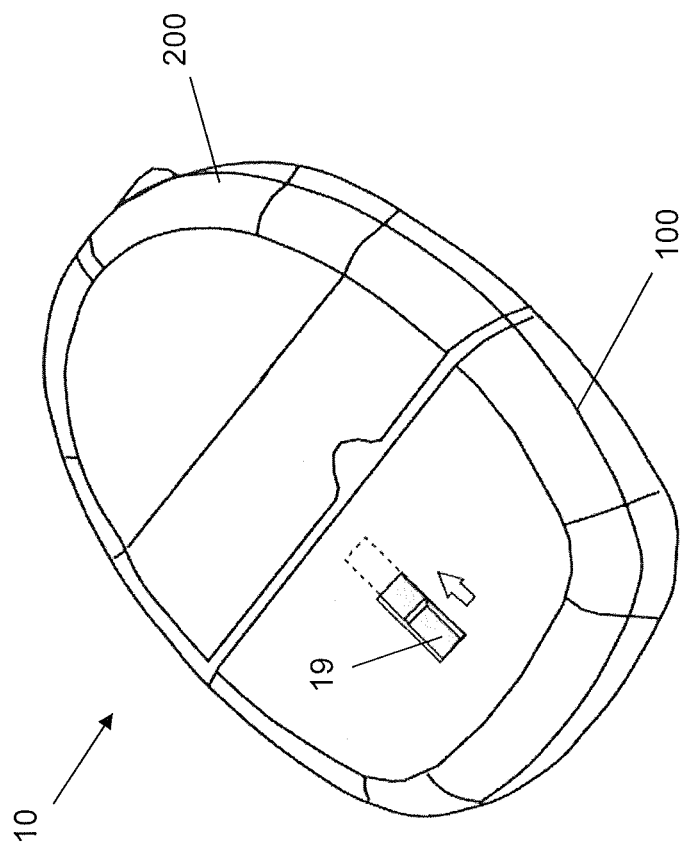
FIG. 19 shows an embodiment of a dispensing patch unit provided with a single exemplary bolus button.

FIG. 19 shows an embodiment of a two-part dispensing patch unit (10) provided with a single bolus button (19). The bolus button (19) can be positioned in the center of the reusable part's (100) upwardly facing side, or in any other location on the reusable part's (100) housing which is accessible to the patient when the dispensing patch unit (10) is connected to the cradle unit (not shown).

Figure 20A:
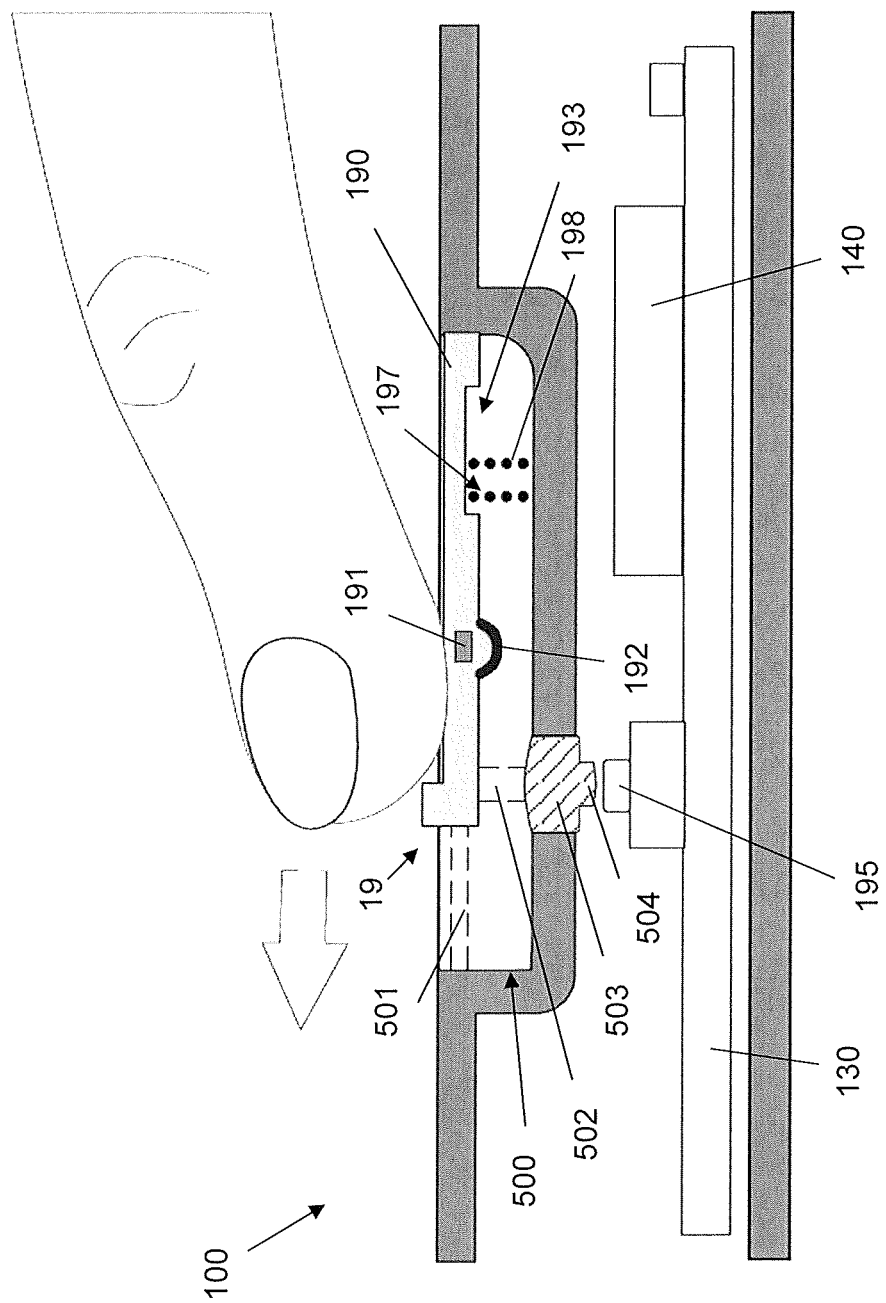
FIGS. 20a-b show cross-sectional views of the exemplary reusable part during the activation of the bolus button.
Figure 20B:
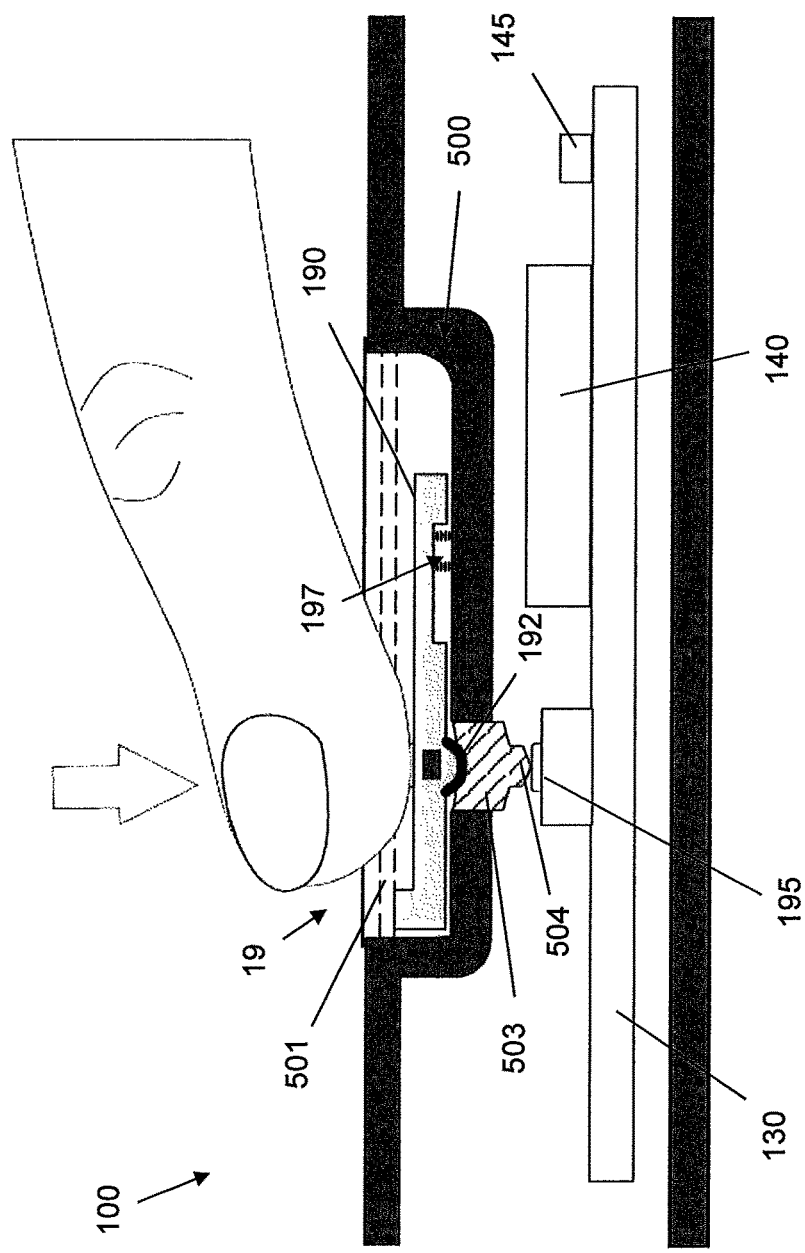

FIGS. 20a-b show cross-sectional views of the reusable part (100) during the activation of the bolus button (19). The reusable part's (100) housing is configured to have an elongated depression (500) provided with at least one horizontal track and one vertical track in each lateral wall of the depression (only one horizontal track and one vertical track are shown, and they are designated by numerals 501 and 502 respectively). A portion (503) of the depression's (500) bottom side is fabricated from a resilient material, e.g. rubber, preferably using an over-molding process. The resilient portion (503) of the depression may have a protrusion (504) protruding inwardly towards the PCB (130). The bolus button (19) comprises a slidable portion (190), which is preferably fabricated from a relatively rigid material, e.g. plastic, and an electronic switch (195), which can be, for example, a commercially available tactile switch (e.g. a tact switch manufactured by Alps Electric Co., Ltd., Japan), or any other electronic switch. The electronic switch (195) is soldered to the PCB (130) and connected to the CPU (140). The slidable portion (190) has at least two lateral projections, oppositely positioned, which fit inside the tracks (501, 502) in the lateral walls of the depression (500), and can move along said tracks. Said projections are not shown, however a rectangular mark (191) indicates one possible location of the projections on the slidable portion's (190). The slidable portion (190) has in addition a protrusion (192) on its inwardly facing side.

The bolus button (19) can be provided with two springs (197, 198). A first spring (197) is preferably attached in one end to the bottom side of the slidable portion (190), inside a dedicated depression (193), and in the other end to the reusable part's (100) housing. A second spring (198) is preferably attached in one end to the bottom side of the slidable portion (190), surrounding the protrusion (192), while its other end is not attached to any other component.

In order to initiate bolus delivery, the patient is required to move the slidable portion (190) of the bolus button (19) along the horizontal tracks (501), as shown in FIG. 20a, until the slidable portion (190) reaches the end of the depression (500). Only then can the patient push the slidable portion (190) downwardly along the vertical tracks (502), as shown in FIG. 20b. Thus it is ensured that the bolus button (19) cannot be pressed unintentionally.

The horizontal movement of the slidable portion (190) causes the first spring (197) to stretch diagonally. As the slidable portion (190) is being pushed downwardly, the second spring (198) is constricted against the reusable part's (100) housing, allowing the inwardly facing protrusion (192) of the slidable portion (190) to push downwardly the resilient portion (503) of the reusable part's (100) housing. The resilient portion (503) then pushes the electronic switch (195) with its protrusion (504), thus turning the switch (195) on. When the CPU (140) is signaled that the electronic switch (195) is in an "ON" state, it activates the motor such that a bolus dose of therapeutic fluid (e.g. insulin) is delivered. The CPU (140) is also preferably programmed to indicate to the patient, via the notification component (145), whether bolus delivery has been initiated or not.

When the patient lifts his finger off the bolus button's slidable portion (190), the resilient portion (503) of the reusable part's (100) housing disengages from the electronic switch (195). The second spring (198) stretches back to its initial position, thus pushing upwardly the slidable portion (190) of the button (19). The first spring (197) can then constrict back to its initial position, while pulling the slidable portion (190) backwards along the horizontal tracks (501), until it is returned to its initial position.

Figure 21:
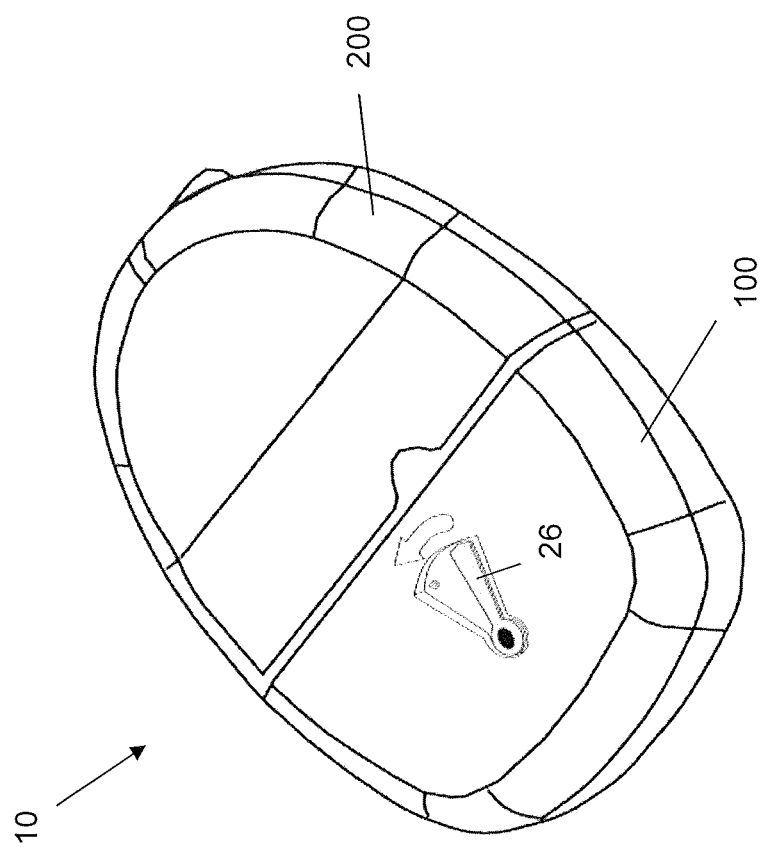
FIG. 21 shows another embodiment of an exemplary dispensing patch unit provided with an exemplary single bolus button.

FIG. 21 shows another embodiment of a dispensing patch unit (10) provided with a single bolus button (26). In this embodiment the patient is required to rotate a rotatable portion of the bolus button (26) prior to pressing it, thus ensuring that the button (26) cannot be pressed unintentionally.

Figure 22A:
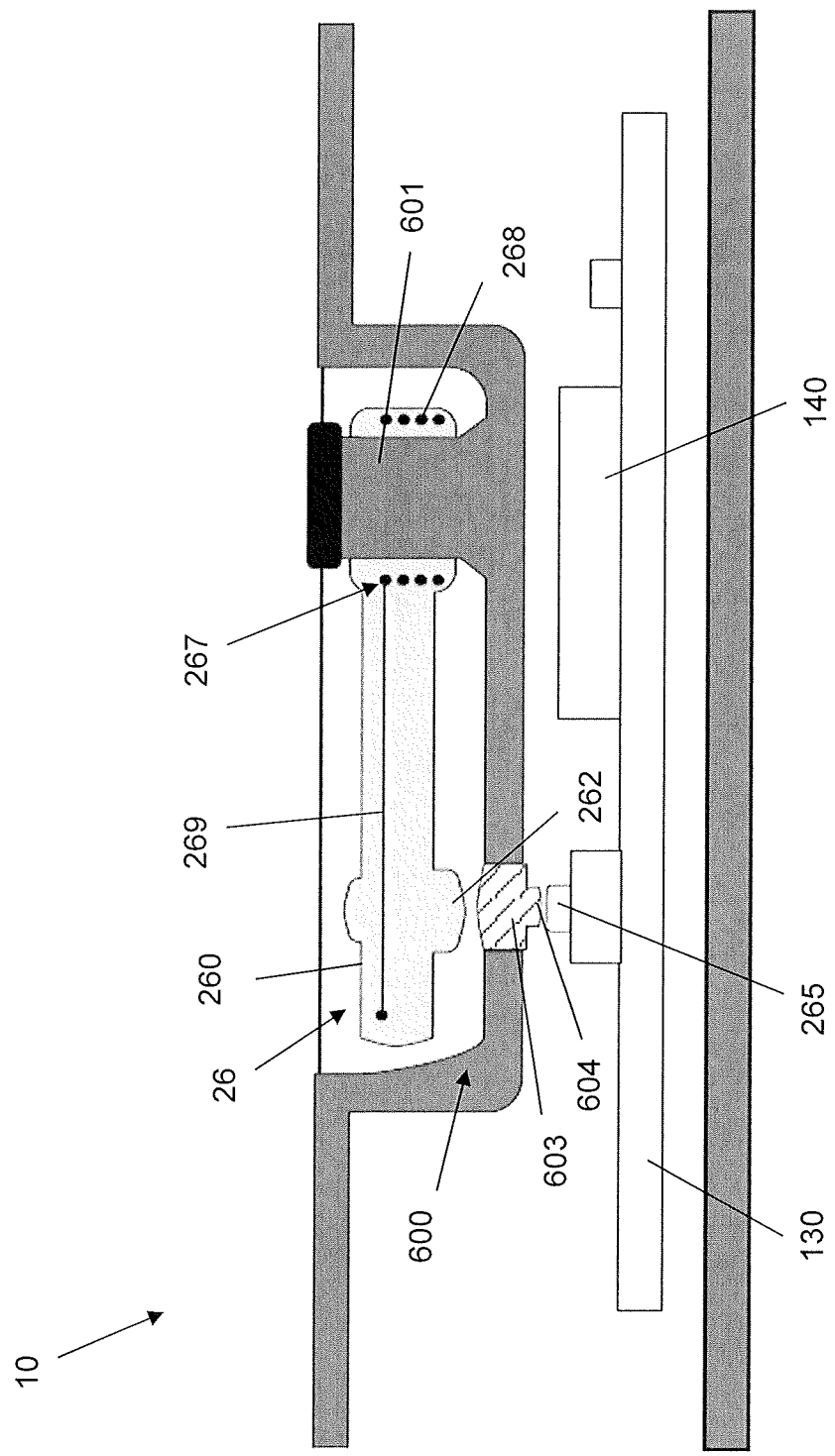
FIGS. 22a-b show cross-sectional views of the reusable part during the activation of the exemplary bolus button.
Figure 22B:
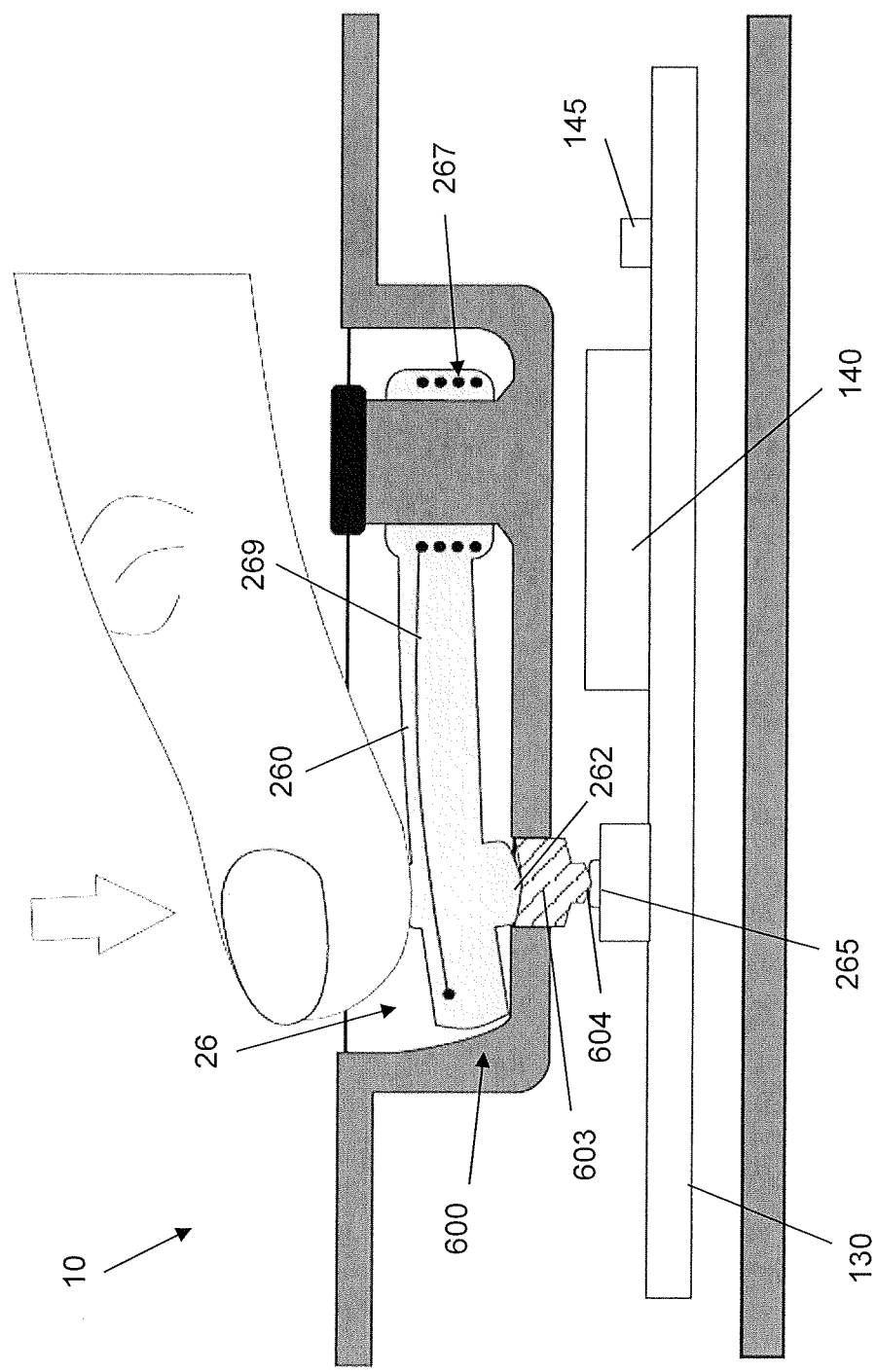

FIGS. 22a-b show cross-sectional views of the reusable part (100) during the activation of the bolus button (26). The button (26) comprises a rotatable portion (260) and an electronic switch (265), which can be, for example, a commercially available tactile switch (e.g. a tact switch manufactured by Alps Electric Co., Ltd., Japan), or any other electronic switch. The electronic switch (265) is soldered to the PCB (130) and connected to the CPU (140). The bolus button (26) is also provided with a torsion spring (267). The torsion spring's coil portion (268), as well as one of its legs (269), is embedded in the rotatable portion (260) of the bolus button (26), whereas the second leg (not shown) is embedded in the reusable part's (100) housing. The reusable part's (100) housing is configured to have a dedicated depression (600), which accommodates the rotatable portion (260) of the bolus button (26). The rotatable portion (260) is fixed to the reusable part's (100) housing by means of a dedicated hinge (601) located in the depression (600). A small portion (603) of the depression's (600) bottom side is fabricated from a resilient material, e.g. rubber, preferably using an over-molding process. The resilient portion (603) of the depression may have a protrusion (604) protruding inwardly towards the PCB (130).

In order to initiate a bolus delivery, the patient is required to rotate the rotatable portion (260) of the bolus button (26) until it reaches the opposite side of the depression (600). FIG. 22a shows a cross-sectional view of the reusable part (100) after the rotatable portion (260) of the bolus button (26) has been rotated. It is not shown but it should be appreciated that rotational movement of the rotatable portion (260) loads the torsion spring (267).

FIG. 22b shows the patient pushing down the rotatable portion (260) of the bolus button (26). As the rotatable portion (260) is being pushed down, its inwardly facing protrusion (262) pushes downwardly the resilient portion (603) of the reusable part's (100) housing, which in turn pushes the electronic switch (265) with its protrusion (604), thus turning the switch (265) on. When the CPU (140) is signaled that the electronic switch (265) is in an "ON" state, it activates the motor such that a bolus dose of therapeutic fluid (e.g. insulin) is delivered. The CPU (140) is also preferably programmed to indicate to the patient, via the notification component (145), whether bolus delivery has been initiated or not.

When the patient lifts his finger off the bolus button's rotatable portion (260), the resilient portion (603) of the reusable part's (100) housing disengages from the electronic switch. The torsion spring (267) then unwinds, rotating the rotatable portion (260) back to its initial position.

It will be noted, that a button may alternatively be set up such that pressing the button would place the switch in an "OFF" state (i.e., disconnecting one or more "status" circuits within the unit).

Other embodiments of a single bolus button may include a bolus button the operation of which is based on capacitive sensing, or a bolus button the operation of which is based on the Hall Effect, etc. Alternative safety mechanisms may include, for example, a moveable safety cap provided in the dispensing patch unit's housing, etc.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

Any and all of the foregoing patents, applications, and publications referenced in this specification are hereby incorporated by reference herein in their entireties.

What is claimed is:

1. A portable therapeutic fluid delivery device for delivering a therapeutic fluid into a body of a patient comprising:
   a reservoir for containing the therapeutic fluid;
   a dispensing mechanism for dispensing the therapeutic fluid from the reservoir toward the body of the patient;
   a housing configured for securing to the body of the patient, the housing accommodating the reservoir and the dispensing mechanism;
   a first bolus delivery button to initiate the delivery of the therapeutic fluid into the body of the patient;
   a second bolus delivery button to initiate the delivery of the therapeutic fluid into the body of the patient; and
   a processor configured to active the dispensing mechanism, wherein the initiation of the bolus dosage delivery requires that the two buttons must be pressed simultaneously such that a signal is sent to the processor which activates the dispensing mechanism based on the simultaneous press of both buttons, thus ensuring that the bolus delivery cannot be initiated unintentionally.

2. The device of claim 1 further comprising a locking mechanism adapted for preventing the patient from inadvertently activating the first and the second bolus delivery button for the delivery of the therapeutic fluid into the body of the patient unless the locking mechanism is put in an unlocked position.

3. The device of claim 2 wherein the cradle unit comprises a dedicated fluid passage.

4. The device of claim 1 further comprising a cradle unit adherable to a skin of the patient.

5. The device of claim 1 wherein the dispensing mechanism comprises a syringe-type pumping mechanism.

6. The device of claim 1 wherein the dispensing mechanism comprises a plunger comprising a plunger rod.

7. The device of claim 1 wherein the two bolus delivery buttons are located oppositely from each other on the lateral walls of the housing.

8. The device of claim 1 wherein each of the two bolus delivery buttons include a button portion and a button contact, said button portion having a protrusion configured to be positioned in close proximity to the button contact when not pressed and in contact with the button contact when pressed.

9. The device of claim 8, wherein the button portion fits into a concave portion of the button contact.

10. The device of claim 8, wherein the button contact is a metal strip.

11. The device of claim 10, wherein the metal strip is configured to engage with a conductive pad when pressed to form a contact switch.

12. The device of claim 1, wherein upon the two buttons being pressed simultaneously a closed circuit is formed which causes the processor to activate the dispensing mechanism.

13. The device of claim 1, wherein upon the two buttons being pressed simultaneously an open circuit is formed which causes the processor to activate the dispensing mechanism.

14. The device of claim 1, wherein the dispensing mechanism comprises a motor.

15. The device of claim 1, wherein each of the two bolus delivery buttons comprises a protrusion on an inwardly facing side and the protrusion is configured to push a switch for the initiation of the delivery of the therapeutic fluid when the two bolus delivery buttons are pressed inwardly.

16. The device of claim wherein each of the two bolus delivery button is configured of a plastic and a metal strip.

* * * * *